(12) United States Patent
Root et al.

(10) Patent No.: US 7,195,882 B2
(45) Date of Patent: Mar. 27, 2007

(54) MONOCLONAL ANTIBODIES SPECIFIC FOR BUPRENORPHINE AND METABOLITES THEREOF

(75) Inventors: Richard T. Root, Fishers, IN (US); Mitali Ghoshal, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 187 days.

(21) Appl. No.: 10/453,256

(22) Filed: Jun. 3, 2003

(65) Prior Publication Data

US 2004/0248222 A1    Dec. 9, 2004

(51) Int. Cl.
*C01N 33/535*    (2006.01)
*C01N 33/533*    (2006.01)
*C07K 16/44*    (2006.01)
*C07K 17/06*    (2006.01)
*C07D 451/00*    (2006.01)

(52) U.S. Cl. ............ 435/7.93; 435/7.94; 435/7.95; 436/527; 436/531; 436/545; 436/546; 530/388.9; 530/403; 530/404; 530/405; 530/406; 546/46

(58) Field of Classification Search ............ 530/403, 530/404, 405, 406, 388.9; 435/7.93, 7.94, 435/7.95; 436/545, 546, 527, 531, 46
See application file for complete search history.

(56) References Cited

U.S. PATENT DOCUMENTS

| 4,833,073 A | 5/1989 | McNally et al. | ............ 435/7 |
| 5,292,899 A | 3/1994 | Tius et al. | ............ 549/390 |
| 5,908,927 A | 6/1999 | Nguyen et al. | ............ 536/28 |

FOREIGN PATENT DOCUMENTS

WO    2004/036227 A1 *    4/2004

OTHER PUBLICATIONS

V. Cirimele et al, J. Analytical Toxicology, vol. 27, pp. 103-105 (2003).*
Pope, L. et al., "Specific buprenorphine assay using CEDIA® technology," Clinical Chemistry, vol. 49, No. 6, Supplement, Jul. 24, 2003, E-19.
Barlett, A. J. et al., "The Radioimmunoassay of Buprenorphine," Eur. J. Clin. Pharmacol., 18, 339-345 (1980).
Debrabandere, L. et al., "Development of a Radioimmunoassay for the Determination of Buprenorphine in Biological Samples," Analyst, Feb. 1993, vol. 118, pp. 137-143.
Hackett, L. P. et al., Journal of Chromatography, 374 (1986) 400-404.
Hand, C. W. et al., "Radioimmunoassay of buprenorphine with iodine label: analysis of buprenorphine and metabolites in human," Ann. Clin. Biochem., 23: 47-53. (1986).
Hand, C. W. et al., "Radioimmunoassay of Buprenorphine in Urine: Studies in Patients and in a Drug Clinic," Journal of Analytic Toxicology, vol. 13, Mar./Apr. 1989, pp. 100-104.
Moody, D. et al., "Determination of Buprenorphine in Human Plasma by Gas Chromatography-Positive Ion Chemical Ionization Mass Spectrometry and Liquid Chromatography-Tandem Mass Spectrometry," Journal of Analytical Toxicology, vol. 21, Oct. 1997.

* cited by examiner

*Primary Examiner*—Mary E. Ceperley
(74) *Attorney, Agent, or Firm*—Marilyn L. Amick; Roche Diagnostics Operations, Inc.

(57) ABSTRACT

The present invention relates to monoclonal antibodies that specifically bind buprenorphine and/or at least one metabolic product thereof. The present invention further relates to buprenorphine metabolite conjugates for the production of monoclonal antibodies that specifically bind buprenorphine and/or at least one metabolic product thereof and hybridoma cells that produce the monoclonal antibodies. The invention also relates to immunoassay methods for determining buprenorphine and/or one or more buprenorphine metabolites in a sample using the novel antibodies and conjugates of the present invention.

12 Claims, 9 Drawing Sheets

A. Buprenorphine

B. Norbuprenorphine

C. Buprenorphine-3-O-glucuronide

D. Norbuprenorphine glucuronide

MONOCLONAL ANTIBODIES SPECIFIC FOR BUPRENORPHINE AND METABOLITES THEREOF

FIELD OF THE INVENTION

The present invention relates to monoclonal antibodies that specifically bind buprenorphine and/or one or more metabolic products thereof. In addition, the present invention relates to methods for producing the monoclonal antibodies, methods of using the monoclonal antibodies, and kits comprising the monoclonal antibodies. The present invention further relates to buprenorphine or buprenorphine metabolite conjugates for the production of monoclonal antibodies that specifically bind buprenorphine and/or one or more metabolic products thereof and hybridoma cells that produce the monoclonal antibodies of the invention.

BACKGROUND OF THE INVENTION

Buprenorphine, N-cyclopropylmethyl-7α-[1-(5)-hydroxy-1,2,2-trimethylpropyl]-6,14-endo-ethano-6,7,8,14-tetrahydronoripavine, is a highly lipophylic opiate analog with both agonist and antagonist properties at the μ-opiate receptor (Martin et al., *J. Pharmacol. Exp. Ther.*, 197:517 (1976); Cowan et al., *Br. J. Pharmacol.*, 60: 537 (1977); Heel et al., *Drugs*, 17:81 (1979)). As an analgesic, it has a potency about 30 times higher than that of morphine and 75 times higher than that of pentazocine when administered intravenously or intramuscularly and is effective in the treatment of acute and chronic pain. Buprenorphine has a long duration of action because it dissociates slowly from the buprenorphine-receptor complex (Hambrook et al., *Opiates and Endogenous Opiate Peptides*, 295–301 (1976)). Another important feature of the drug is its limited effect on respiration, even in overdose (Hand et al., *Ann. Clin. Biochem.*, 23: 47–53 (1986); Banks et al., *N.Z. Med. J.*, 89: 256–257 (1979)). Due to its potency and other beneficial properties, buprenorphine is used broadly for pain management in, for example, cancer and postoperative patients.

Further, due to its long duration of action, its ability to antagonize opiates, its low dependence liability and lack of significant withdrawal symptoms compared to heroin, cocaine, and other narcotics, buprenorphine is also useful in the management of opiate dependency, including the rehabilitation of opiate addicts (Jasinski et al., *Arch. Gen. Psychiatry*, 35:501 (1978); Mello et al., *Science*, 207: 657 (1980)). Nevertheless, despite its lower physical dependence liability, buprenorphine abuse has been reported (Strang, *Lancet*, 25: 725 (1985); Robertson et al., *Br. Med. J.*, 292: 1465 (1986); Chowhurdy et al., *Br. J. Addiction*, 85: 1349 (1990)).

The chemistry of buprenorphine metabolism in man and other animals (e.g., canine and equine) has been well-studied, with the kinetics reported in plasma (Hand et al., *Ann. Clin. Biochem.*, 23: 47–53 (1986); McQuay et al., *Advances in Pain Research and Therapy*, pp. 271–278 (1986); Bullingham et al., *Clin. Pharmacokinet.*, 8: 332–343 (1983)) and in urine (Cone et al., *Drug Metab. Dispos.*, 12: 577–581 (1984); Hand et al., *J. Anal. Tox.*, 13: 100–104 (1989); Heel et al., *Drugs*, 17: 81 (1979)) after intravenous, intramuscular, and sublingual administration. The parent drug is nearly completely metabolized to norbuprenorphine, norbuprenorphine 3-O-β-D-glucuronide (norbuprenorphine glucuronide), and buprenorphine 3-O-β-D-glucuronide (buprenorphine glucuronide) and is consequently present in urine at extremely low concentrations. After sublingual administration, buprenorphine plasma concentrations rise slowly and are maintained at low concentrations for several hours (Bullingham et al., *Br. J. Clin. Pharmacol.*, 13: 665–673 (1982)). Buprenorphine has a long half-life of about 8 hours, and the norbuprenorphine metabolite appears to have an even slower elimination (Hand et al., *Ann. Clin. Biochem.*, 23: 47–53 (1986); McQuay et al., *Advances in Pain Research and Therapy*, pp. 271–278 (1986); Bullingham et al., *Clin. Pharmacokinet.*, 8: 332–343 (1983)). This accords with the appearance of buprenorphine and its buprenorphine glucuronide metabolite in urine in 1–2 days and norbuprenorphine and norbuprenorphine glucuronide in 1–4 days (Cone et al., *Drug Metab. Dispos.*, 12: 577–581 (1984); Blom et al., *J. Chromatogr.*, 338: 89–98 (1985)). Heel et al. reports that approximately 15–27% of a dose of buprenorphine appears in the urine, mainly in the form of glucuronide metabolites of the parent compound and the norbuprenorphine metabolite (Heel et al., *Drugs*, 17:81 (1979)).

The accurate detection of buprenorphine and its metabolites in a biological sample, such as plasma or urine, is useful for several purposes, including determining the illicit use or abuse of buprenorphine, monitoring the dose and efficacy of buprenorphine during clinical treatment for pain, and confirming the prescriptive use of buprenorphine, for example, confirming its use in a drug rehabilitation program. Furthermore, given that the criteria of assay performance for one use may not be applicable for other uses, the differential detection of buprenorphine and its metabolites, i.e., an assay that distinguishes between buprenorphine and buprenorphine metabolites, is useful. For example, confirmation of appropriate rehabilitative use of buprenorphine requires the accurate detection of buprenorphine metabolites rather than buprenorphine in urine, as the presence of significant amounts of the unmetabolized parent drug in a urine sample indicates patient tampering, i.e., adulteration of the sample with buprenorphine to feign compliance with the rehabilitation program. Thus, an assay for the sensitive detection of a buprenorphine metabolite is required to accurately confirm rehabilitative use of buprenorphine. In some cases, it is critical to accurately measure only the parent drug. For example, when buprenorphine is used for the management of pain, only plasma levels of the parent drug are relevant (D. Moody et al., J. Anal. Toxicol. 21:406–414, 1997). In other instances, it is appropriate to measure either the parent drug or its metabolites, or both the parent drug and its metabolites. For example, the determination of buprenorphine abuse in humans and other mammalian subjects can be made by detecting the presence of buprenorphine and/or one or more of its metabolic products.

Current methods for the detection of buprenorphine and its metabolites include chromatographic methods, including thin layer chromatography, gas chromatography and high-performance liquid chromatography, which can be used to detect the parent drug buprenorphine (Hackett et al., *J. Chromatography*, 374: 400–404 (1986)). However, these methods can be time-consuming and expensive and can also lack the sensitivity required for the accurate quantitation of buprenorphine and/or its metabolites.

More recently, fluorometric or radiometric immunoassays employing the use of a polyclonal antisera that binds to buprenorphine and/or its metabolites have also been used for the detection of these compounds in biological samples. However, current immunoassays are limited by the sensitivity and/or cross-reactivity of the polyclonal antisera used. Cross-reaction of antisera with metabolites can cause lack of specificity in the measurement of buprenorphine in the absence of extraction steps to overcome metabolite interference, which may result in an overestimate of buprenorphine concentration (Bartlett et al., *Eur. J. Clin. Pharmacol.*, 18: 339–345 (1980); Debrabandere et al., *Analyst*, 118:137–143 (1993)). Debrabandere et al. describes a polyclonal antibody that cross-reacts with buprenorphine and norbuprenorphine such that it can not distinguish between the parent drug and the metabolite (Debrabandere et al., *Analyst*, 118:137–143 (1993)) Further, the polyclonal antibody fails to recognize the buprenorphine glucuronide metabolite.

Other groups have described the use of polyclonal antibodies cross-reactive with buprenorphine and a specific metabolite thereof, i.e., norbuprenorphine or buprenorphine glucuronide (Bartlett et al., *Eur. J. Clin. Pharmacol.*, 18: 339–345 (1980); Hand, et al., *Ann. Clin. Biochem.*, 23: 47–53 (1986); Hand et al., *J. Anal. Tox.*, 13: 100–104 (1989)). As is the case generally, the above-mentioned polyclonal antibodies were raised by immunizing a mammal with a conjugate of the particular buprenorphine metabolite of interest (or a derivative thereof). The resulting polyclonal antibodies demonstrate a limited cross-reactivity to other metabolites, as well as to buprenorphine, relative to the particular metabolite used for immunization. Thus, the sensitivity of the polyclonal antibodies for buprenorphine is diminished. Furthermore, producing a polyclonal antibody specific for a particular buprenorphine metabolite can be difficult given that it requires procurement of a sufficient amount of the specific metabolite for preparation of an immunogen conjugate, which metabolite may not be commercially available and may be burdensome to synthesize.

SUMMARY OF THE INVENTION

The present invention relates to monoclonal antibodies that specifically bind to buprenorphine and/or one or more buprenorphine metabolites. The monoclonal antibodies provided in the present invention each have different specific binding characteristics, including: (1) the ability to specifically bind buprenorphine without cross-reactivity to its metabolites; (2) the ability to specifically bind buprenorphine and one or more buprenorphine metabolites; or (3) the ability to specifically bind a specific buprenorphine metabolite without cross-reactivity to the parent drug or another buprenorphine metabolite, which binding characteristics allow the monoclonal antibodies to be effectively employed in a variety of applications. The monoclonal antibodies provided herein have binding affinities that allow them to detect a low concentration of buprenorphine and/or one or more buprenorphine metabolites in a sample and specificities that allow them to differentially resolve buprenorphine or one or more specific metabolites of buprenorphine.

The present invention also provides immunogen conjugates and methods for generating the monoclonal antibodies of the invention. The invention provides a novel method for producing monoclonal antibodies specific for one or more buprenorphine metabolites using a derivative of the parent drug to prepare an immunogen conjugate and selecting for monoclonal antibodies specific for the metabolites of interest. The method is advantageous in that the parent drug buprenorphine conjugate is used as an immunogen to produce monoclonal antibodies that specifically bind one or more buprenorphine metabolites, thereby eliminating the need to use the metabolite in the preparation of an immunogen.

The present invention further relates to methods for using the novel monoclonal antibodies to detect buprenorphine and/or one or more buprenorphine metabolites in a sample and kits comprising the novel monoclonal antibodies. The ability of the monoclonal antibodies to differentially detect buprenorphine or one or more buprenorphine metabolites is useful given that the criteria for one use may not be applicable for other uses. For example, confirmation of appropriate rehabilitative use of buprenorphine requires the accurate detection of buprenorphine metabolites in urine rather than buprenorphine. Monitoring buprenorphine levels in pain management requires the accurate detection of buprenorphine only. However, the determination of buprenorphine abuse can be made by detecting the presence of buprenorphine and/or one or more of its metabolic products.

In one embodiment, the invention provides a buprenorphine metabolite conjugate having the structure

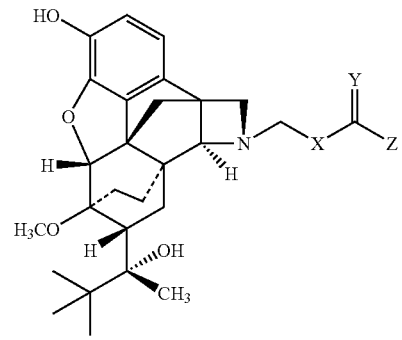

wherein X is a linking group consisting of 0–10 carbon atoms or heteroatoms including 0–2 substituted or unsubstituted aromatic rings, Y is O, NH, or S, and Z is a leaving group, poly(amino acid), protein, polysaccharide, or label.

Norbuprenorphine metabolite conjugates having the above structure are advantageous in that they are derived from a novel N-alkylated buprenorphine derivative, which structure is closer to the structure of buprenorphine than previously described N-acylated derivatives of buprenorphine. In one embodiment, the norbuprenorphine metabolite conjugate is norbuprenorphine-KLH, in which the KLH is covalently attached through a linker to the nitrogen atom (N17) of norbuprenorphine. In another embodiment, the norbuprenorphine conjugate is norbuprenorphine-BSA, in which the BSA is covalently attached through a linker to the nitrogen atom (N17) of norbuprenorphine.

BRIEF DESCRIPTION OF THE DRAWINGS

FIG. 1A shows the chemical structure of buprenorphine; FIG. 1B shows the chemical structure of norbuprenorphine; FIG. 1C shows the chemical structure of buprenorphine glucuronide; and FIG. 1D shows the chemical structure of norbuprenorphine glucuronide.

DETAILED DESCRIPTION OF THE INVENTION

Figure 1:
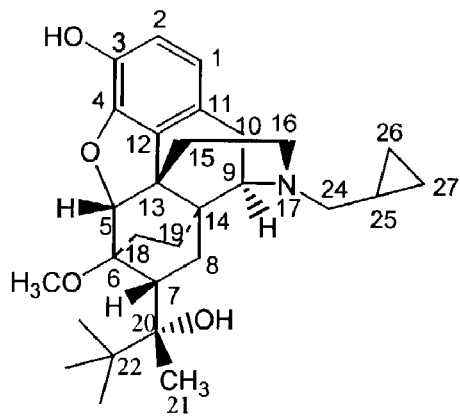
FIG. 1 provides the chemical structures of buprenorphine and several of its metabolic products.
Figure 1:
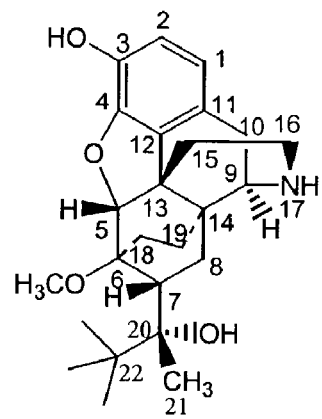
Figure 1:
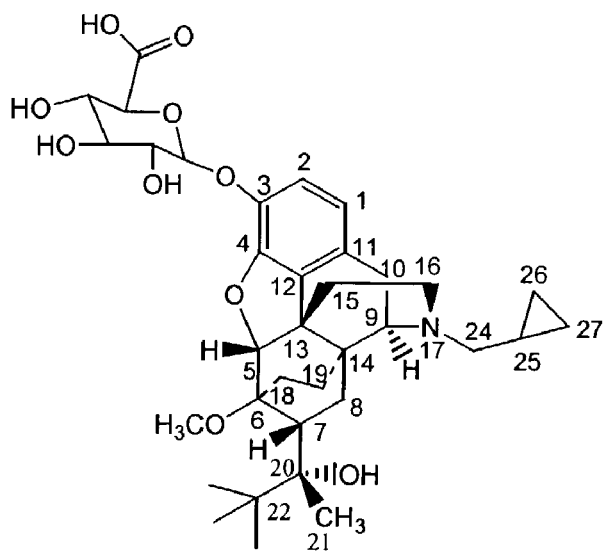
Figure 1:
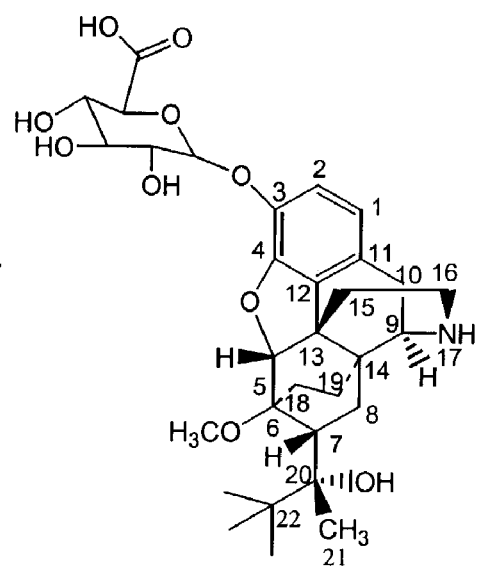

The section headings used herein are for organizational purposes only and are not to be construed as limiting the subject matter described. All references cited in this application are expressly incorporated by reference herein.

Definitions

As utilized in accordance with the present disclosure, the following terms, unless otherwise indicated, shall be understood to have the following meanings:

The term "$ED_{50}$" as it is used in competitive immunoassay technique herein, refers to the measure of the effective concentration of free competitor antigen required to inhibit monoclonal antibody binding to substrate-bound antigen by 50%. In general, the substrate-bound antigen is buprenorphine or a buprenorphine conjugate, e.g., buprenorphine-BSA or buprenorphine-KLH; however, the substrate-bound antigen can also be a buprenorphine metabolite or a conjugate thereof. The $ED_{50}$ is calculated by measuring antibody binding (constant amount of antibody) to the substrate-bound antigen (e.g., buprenorphine-BSA) over a range of concentrations of competing free antigen (e.g., buprenorphine, buprenorphine metabolite, or opiate). At zero concentration of competing free antigen, maximum binding to the substrate-bound antigen is observed, which binding is measured at $OD_{450}$. At the highest concentration of competing free antigen, minimum binding to the substrate-bound antigen is observed, which binding is measured at $OD_{450}$. The effective range of the measurement is the difference between the observed maximum binding to the substrate-bound antigen ($OD_{450}$ value in the presence of no free competitor antigen) and the observed minimum binding to the substrate-bound antigen ($OD_{450}$ value in the presence of the highest concentration of competitor antigen). The $ED_{50}$ value is calculated by determining the concentration of free competitor antigen that reduces the binding to substrate-bound antigen by 50% over the effective range of measurement. $ED_{50}$ values provide an estimation of the relative binding affinity (i.e., binding strength) of a monoclonal antibody for various antigens, e.g., buprenorphine and buprenorphine metabolites. In general, given comparable titer evaluations, an antigen with a lower $ED_{50}$ value indicates that the antibody has a higher binding affinity for that antigen in comparison to an antigen having a higher $ED_{50}$ value. Therefore, the $ED_{50}$ value for a given antigen can be used to rank affinities by calculating $\log (1/ED_{50})$. The higher the rank, the higher the binding affinity of the monoclonal antibody for the antigen. Given a graph in which $OD_{450}$ values are plotted versus antigen concentrations (molar) for different antigens, the antigen giving a curve to the left of other antigen curves is bound with a higher affinity by the antibody.

The term "specific binding" as used herein is meant to refer to antibody recognition of its target antigen in a complex mixture of buffers, media, proteins, and/or macromolecules. As used herein, an antibody is said to specifically bind an antigen (i.e., buprenorphine, buprenorphine metabolite, or opiate) when the $ED_{50}$ of the antigen (i.e., the concentration of free antigen competitor required to inhibit monoclonal antibody binding to buprenorphine by 50%) is less than 0.1 of the $ED_{50}$ of a standard (i.e., the concentration of free standard competitor required to inhibit monoclonal antibody binding to buprenorphine by 50%). Alternatively, if the $ED_{50}$ of the antigen is more than 0.1 or 10% of the $ED_{50}$ of the standard, then the antigen is said to be "cross-reactive", i.e., significantly cross-reactive. In other words, 10% is the cut-off level for something to be called cross-reactive as the term is used in describing the present invention. As used herein, the standard is generally buprenorphine; however the standard can also be the competitor antigen with the lowest $ED_{50}$ value, including, for example, buprenorphine glucuronide, norbuprenorphine, or norbuprenorphine glucuronide. Stated another way, an antibody is said to specifically bind to an antigen (i.e., buprenorphine, buprenorphine metabolite, or opiate) when the $ED_{50}$ antigen/$ED_{50}$ standard is less than 0.1. If the $ED_{50}$ antigen/$ED_{50}$ standard is greater than 0.1, the binding of the monoclonal antibody to the antigen is not considered to be specific binding.

The term "cross-reactivity" or "significant cross-reactivity" as used herein is meant to refer to the ratio of the value for $ED_{50}$ of the standard used versus the value for $ED_{50}$ of the antigen of interest, i.e., $ED_{50}$ antigen/$ED_{50}$ standard. For purposes herein, a monoclonal antibody is said to be "cross-reactive" with one or more antigens if the monoclonal antibody specifically binds to the antigen(s). In other words, a monoclonal antibody is said to be "cross-reactive" with one or more antigens if the $ED_{50}$ antigen/$ED_{50}$ standard is greater than 0.1 or is greater than 10%. For example, if the standard is buprenorphine, a monoclonal antibody that specifically binds buprenorphine is said to be cross-reactive with a buprenorphine metabolite if the $ED_{50}$ buprenorphine metabolite/$ED_{50}$ buprenorphine is greater than 0.1 or 10%. Likewise, if the standard is buprenorphine, a monoclonal antibody that specifically binds buprenorphine is not cross-reactive with a buprenorphine metabolite if the $ED_{50}$ buprenorphine metabolite/$ED_{50}$ buprenorphine is less than 0.1 or 10%.

The term "monoclonal antibody" is meant to refer to immunoglobulins which arise from a single clone of B-lymphocyte cells and which are initially obtained by fusing a single B-lymphocyte with a hybridoma tumor cell.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, urine, tears, cells, organs, tissues, bone, bone marrow, lymph, lymph nodes, synovial tissue, chondrocytes, synovial macrophages, endothelial cells, and skin.

The term "hapten" refers to partial or incomplete antigens. They are protein-free substances, mostly low molecular weight substances, which are not capable of stimulating antibody formation, but which do react with antibodies. The latter are formed by coupling a hapten to a high molecular weight carrier and injecting this coupled product into mammals. Buprenorphine and buprenorphine metabolites are examples of haptens.

The term "immunogen" is meant to refer to a substance that induces a specific immune response. For example, an immunogen can be a hapten-carrier conjugate in which the hapten (i.e. antigenic molecule) has been covalently attached to a carrier (i.e., immunogenic molecule).

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain poly(amino acid) residues and/or lipid residues.

The immunogenic carrier can also be a poly(nucleic acid) either alone or conjugated to one of the above mentioned poly(amino acids) or polysaccharides.

The immunogenic carrier can also be a particle. The particles are generally at least about 0.02 microns (μm) and not more than about 100 µm, and usually about 0.05 µm to 10 µm in diameter. The particle can be organic or inorganic, swellable or non-swellable, porous or non-porous, optionally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to a binding partner for an analyte, an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, a receptor, or a radioactive isotope.

An "analyte analog" refers to any substance or group of substances which behaves essentially the same as the analyte with respect to binding affinity of the antibody or binding partner for the analyte and is meant to include buprenorphine derivatives and isomers thereof.

The term "screening agent" as used herein is meant to refer to an agent, i.e., antigen, used in an immunoassay to determine the binding properties of a monoclonal antibody produced by a hybridoma. The screening agent can be buprenorphine or a conjugate thereof, and/or a buprenorphine metabolite or conjugate thereof. A screening agent can be used alone or in combination with any other screening agents to determine the binding properties of a monoclonal antibody produced by a hybridoma. The screening agent(s) can be used in a wide variety of immunoassays described herein and otherwise known in the art and can be bound to a solid substrate and/or free in solution.

The term "linker" refers to a chemical moiety that connects a hapten to a carrier, immunogen, label, tracer or another linker. Linkers may also be used to attach antibodies to labels or solid substrates. Linkers may be straight or branched, saturated or unsaturated carbon chains. They may also include one or more heteroatoms within the chain or at the termini of the chains. By heteroatoms is meant atoms other than carbon which are chosen from the group consisting of oxygen, nitrogen and sulfur. The use of a linker may or may not be advantageous or needed, depending on the specific hapten and carrier pairs. Methods and techniques for the attachment of a linker to an antibody are known in the art. For a good treatise on this subject, the reader is referred to Bioconjugate Techniques, G. Hermanson, Academic Press, 1996.

A "carrier", as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms "conjugate" and "derivative" refer to a chemical compound or molecule made from a parent compound by one or more chemical reactions.

The term "active ester" within the sense of the present invention encompasses activated ester groups which can react with nucleophiles such as, but not limited to, free amino groups of peptides, poly(amino acid)s, polysaccharides or labels under such conditions that no interfering side reactions with other reactive groups of the nucleophile-carrying substance can usefully occur.

The term "leaving group" when used in describing active ester chemistry is the alcohol side product which forms when an active ester reacts with a nucleophile.

Monoclonal Antibodies of the Invention

The present invention provides monoclonal antibodies that specifically bind to buprenorphine and/or one or more buprenorphine metabolites. The monoclonal antibodies provided herein have binding characteristics which allow the antibodies to differentially resolve buprenorphine and/or one or more specific metabolites of buprenorphine. In view of their different binding specificities, the monoclonal antibodies of the invention can be effectively employed in a variety of applications.

Figure 5:
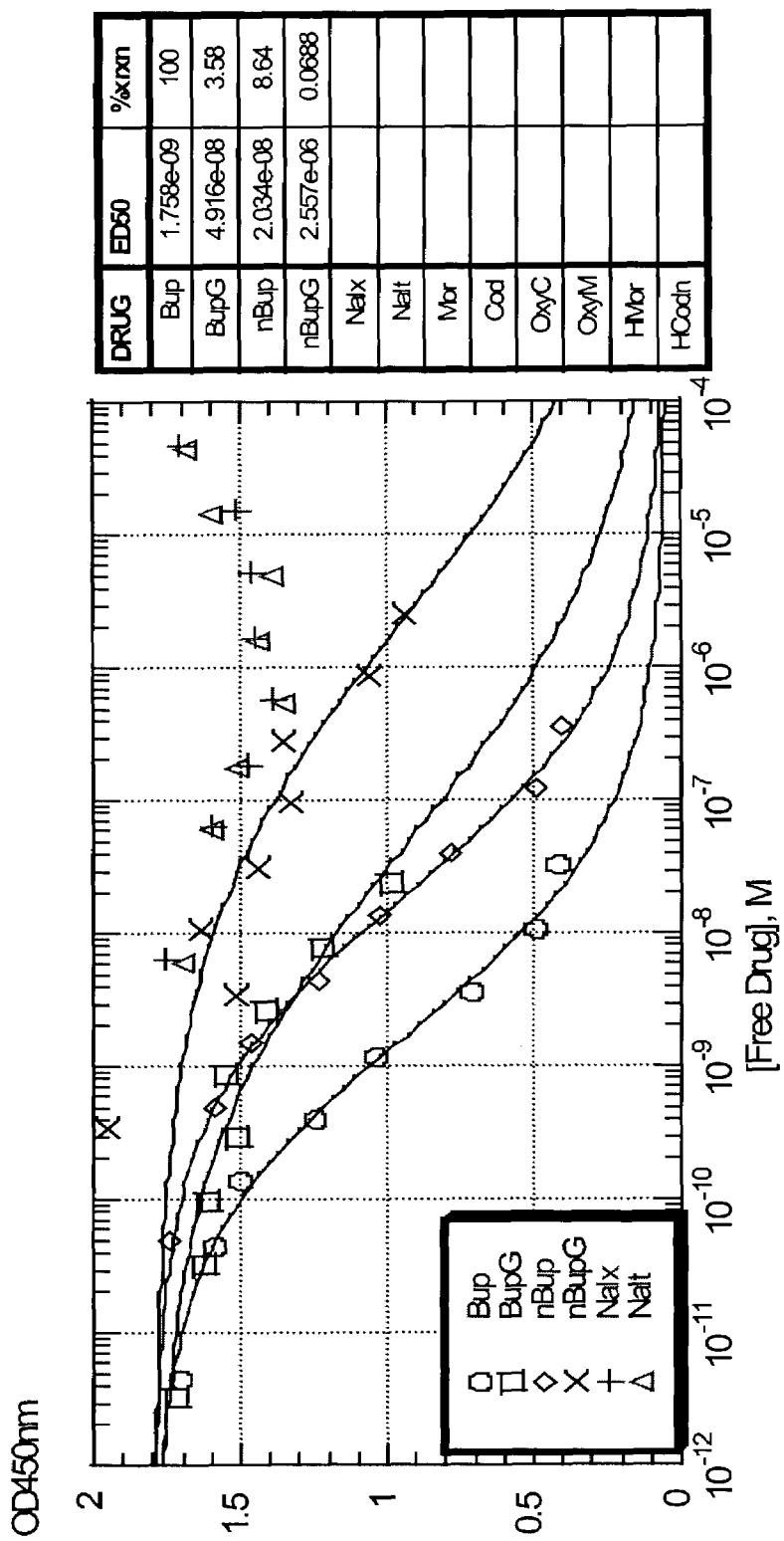
FIG. 5 is a regression plot of the data acquired in competition ELISA binding assays performed for monoclonal antibody BUP 2.2. The amount of monoclonal antibody BUP 2.2 bound to buprenorphine in the presence of various concentrations ($10^{-12}$–$10^{-4}$ M) of free opiate competitors was determined by measuring $OD_{450}$ values in ELISA. Open circles show $OD_{450}$ values in the presence of various concentrations of free buprenorphine. Open squares show $OD_{450}$ values in the presence of various concentrations of free buprenorphine glucuronide. Open diamonds show $OD_{450}$ values in the presence of various concentrations of free norbuprenorphine. X's show $OD_{450}$ values in the presence of various concentrations of free norbuprenorphine glucuronide. Plus symbols show $OD_{450}$ values in the presence of various concentrations of free naloxone. Open triangles show $OD_{450}$ values in the presence of various concentrations of free naltrexone. $ED_{50}$ is the measure of effective concentration of free opiate competitor required to inhibit monoclonal antibody BUP 2.2 binding to buprenorphine by 50%. The cross-reactivity of the monoclonal antibody BUP 2.2 for several buprenorphine metabolites (buprenorphine glucuronide (BupG), norbuprenorphine (nBup), and norbuprenorphine glucuronide (nBupG)) relative to buprenorphine was determined by calculating $ED_{50}$ buprenorphine/$ED_{50}$ buprenorphine metabolite ×100. The monoclonal antibody did not bind to several opiates tested, including naloxone, naltrexone, morphine, codeine, oxycodone, oxymorphone, hydromorphone, and hydrocodone.

In one embodiment, the present invention provides a monoclonal antibody that specifically binds to buprenorphine and does not cross-react with buprenorphine metabolites. The binding properties of exemplary monoclonal antibodies that specifically bind to buprenorphine and do not significantly cross-react with buprenorphine metabolites are shown in FIG. 5 (BUP 2.2) and discussed in Example 4 (BUP 2.2). A hybridoma producing an exemplary clone, BUP 2.2, was deposited with the American Type Culture Collection (ATCC), 10801 University Blvd., Manassa, Va. 20110-2209, on Nov. 1, 2005 (ATCC PTA-7198). Monoclonal antibodies that specifically bind buprenorphine and do not significantly cross-react with buprenorphine metabolites (i.e., BUP 2.2) require the hydroxyl group at C3 and the N-methyl-cyclopropane at N17 for biding. Monoclonal antibodies having these binding characteristics may additionally require the tert-butyl region at C22 for binding. Such monoclonal antibodies are suitable for use in detecting the presence of the parent compound in a sample and can be used to detect opiate abuse.

In another embodiment, the present invention provides a monoclonal antibody that specifically binds one or more buprenorphine metabolites and does not cross-react with buprenorphine. Examples of buprenorphine metabolites that are specifically bound by the monoclonal antibody include buprenorphine glucuronide, norbuprenorphine, and norbuprenorphine glucuronide. In one embodiment, the monoclonal antibody specifically binds one buprenorphine metabolite, for example, buprenorphine glucuronide. An exemplary monoclonal antibody is BUP 88.1.1 (FIG. 6, Example 5), which specifically binds buprenorphine glucuronide with no cross-reactivity to buprenorphine or other buprenorphine metabolites. A hybridoma producing clone BUP 88.1.1, was deposited with the American Type Culture Collection (ATCC), 10801 University Blvd., Manassa, Va. 20110-2209, on Feb. 26, 2003 (ATCC PTA 5023). Another example is monoclonal antibody BUP 67.1 (FIG. 9), which has approximately a 30-fold higher affinity for the buprenorphine glucuronide metabolite than for the parent drug. The monoclonal antibody has no cross-reactivity with norbuprenorphine metabolites. Monoclonal antibodies having these binding characteristics require the glucuronide group at C3 and the N-methyl-cyclopropane at N17 for binding.

In another embodiment, the monoclonal antibody specifically binds norbuprenorphine. Monoclonal antibodies having these binding characteristics require the hydroxyl group at C3 for binding.

In another embodiment, the monoclonal antibody specifically binds norbuprenorphine glucuronide. Monoclonal antibodies having these binding characteristics require the glucuronide group at C3 for binding.

In another embodiment, the monoclonal antibody specifically binds two or more buprenorphine metabolites, including, for example, two or more of the metabolites listed above and does not cross-react with buprenorphine. In one embodiment, the monoclonal antibody specifically binds norbuprenorphine and norbuprenorphine glucuronide. Exemplary monoclonal antibodies BUP 83.1.1 and BUP 42.1 (FIG. 7, Example 6) specifically bind norbuprenorphine with no cross-reactivity to buprenorphine. Antibody BUP 83.1.1 has a 36,000-fold greater affinity for norbuprenorphine than for the parent drug. BUP 83.1.1 has no cross-reactivity with the buprenorphine glucuronide metabolite and low cross-reactivity with norbuprenorphine glucuronide. A hybridoma producing clone BUP 83.1.1, was deposited with the American Type Culture Collection (ATCC), 10801 University Blvd., Manassa, Va. 20110-2209, on Feb. 26, 2003 (ATCC PTA 5022). Monoclonal antibody BUP 42.1 has similar binding characteristics, i.e., it specifically binds to norbuprenorphine with no cross-reactivity to buprenorphine or buprenorphine glucuronide and low cross-reactivity to norbuprenorphine glucuronide. Monoclonal antibodies sharing these binding characteristics require the absence of all or part of the N-methyl-cyclopropane group at N17 and prefer the hydroxyl group at C3 over the glucuronide group for binding.

In another embodiment, the monoclonal antibody specifically binds buprenorphine glucuronide and norbuprenorphine glucuronide. Monoclonal antibodies sharing these binding characteristics require the presence of the glucuronide group at C3 for binding.

Monoclonal antibodies that specifically bind one or more buprenorphine metabolites, such as those described above, are suitable for detecting the presence of the specific buprenorphine metabolites to which they bind. Alone or in combination, such monoclonal antibodies can be used to study the pharmacokinetics of opiate administration. They can also be used to determine buprenorphine abuse and confirm compliance with an opiate rehabilitation program.

In another embodiment, the monoclonal antibody specifically binds buprenorphine and one or more buprenorphine metabolites, for example, norbuprenorphine, norbuprenorphine glucuronide, and buprenorphine glucuronide. In one embodiment, the monoclonal antibody specifically binds buprenorphine and one buprenorphine metabolite. In one embodiment, the monoclonal antibody specifically binds buprenorphine and norbuprenorphine. Monoclonal antibodies having these binding characteristics require the presence of the hydroxyl group at C3 for binding. In another embodiment, the monoclonal antibody specifically binds buprenorphine and norbuprenorphine glucuronide. Monoclonal antibodies having these binding characteristics demonstrate partial recognition of the C3 oxygen. In another embodiment, the monoclonal antibody specifically binds buprenorphine and buprenorphine glucuronide. Several exemplary monoclonal antibodies that bind buprenorphine and buprenorphine glucuronide are shown in Table 3 and described in Example 7. One exemplary clone, BUP 73.2, is produced by a hybridoma deposited with the American Type Culture Collection (ATCC), 10801 University Blvd., Manassa, Va. 20110-2209, on Feb. 26, 2003 (ATCC PTA 5021). The monoclonal antibodies bind buprenorphine and buprenorphine glucuronide with similar affinity and have no cross-reactivity with norbuprenorphine metabolites. Monoclonal antibodies having these binding characteristics demonstrate partial recognition of the C3 oxygen and require the presence of the N-methyl-cyclopropane group at N17 for binding. Another exemplary clone, BUP 21.3, is produced by a hybridoma deposited with the American Type Culture Collection (ATCC), 10801 University Blvd., Manassa, Va. 20110-2209, on Feb. 26, 2003 (ATCC PTA 5020).

In another embodiment, the monoclonal antibody specifically binds buprenorphine and two or more buprenorphine metabolites. In one embodiment, the monoclonal antibody specifically binds buprenorphine, norbuprenorphine and norbuprenorphine glucuronide. In another embodiment, the monoclonal antibody specifically binds buprenorphine, norbuprenorphine glucuronide, and buprenorphine glucuronide. In another embodiment, the monoclonal antibody specifically binds buprenorphine, norbuprenorphine, and buprenorphine glucuronide. In another embodiment, the monoclonal antibody specifically binds buprenorphine, norbuprenorphine, norbuprenorphine glucuronide, and buprenorphine glucuronide. Monoclonal antibodies having the above binding characteristics demonstrate partial recognition of the C3 oxygen. Exemplary monoclonal antibodies are described in Example 7 and FIG. 8. For example, BUP 1.1 binds buprenorphine and buprenorphine glucuronide with approximately equal affinity and has cross-reactivity with norbuprenorphine. Several additional monoclonal antibodies that bind buprenorphine and buprenorphine glucuronide with similar affinity and have low cross-reactivity with norbuprenorphine metabolites are shown in Table 2. Monoclonal antibodies having these binding characteristics demonstrate partial recognition of the C3 oxygen and partial recognition of the N-methyl-cyclopropane group at C9 for binding. Monoclonal antibodies that bind to buprenorphine and one or more buprenorphine metabolites can be used to determine buprenorphine abuse; however, such monoclonal antibodies would not be useful to confirm compliance with an opiate rehabilitation program.

In one embodiment, the monoclonal antibody has a higher binding affinity for buprenorphine than for buprenorphine metabolites. Example 9 (Table 5) describes several exemplary monoclonal antibodies that specifically bind to buprenorphine and cross-react with norbuprenorphine. The monoclonal antibodies do not cross-react with buprenorphine glucuronide metabolites. Monoclonal antibodies having these binding characteristics require the hydroxyl at C3 and recognize the N-methyl-cyclopropane group at N17 for binding.

In another embodiment, the monoclonal antibody has a higher binding affinity for one or more buprenorphine metabolites than buprenorphine. Example 8 (Table 4) describes several exemplary monoclonal antibodies having a higher binding affinity for buprenorphine glucuronide than buprenorphine and no cross-reactivity to norbuprenorphine metabolites or other opiates. Another monoclonal antibody (BUP 4.2) demonstrates similar binding characteristics, i.e., it specifically binds to buprenorphine glucuronide with greater affinity than buprenorphine and has no cross-reactivity to norbuprenorphine metabolites. Monoclonal antibodies having these binding characteristics require the presence of glucuronide at C3 and demonstrate partial or complete recognition of the N-methyl-cyclopropane group at N17 for binding.

The monoclonal antibodies of the invention can be attached to a detectable label. Examples of suitable detectable labels include, but are not limited to, a radioisotope or radionuclide (e.g., $^{3}H$, $^{14}C$, $^{15}N$, $^{35}S$, $^{90}Y$, $^{99m}Tc$, $^{111}In$, $^{125}I$, $^{131}I$), an enzyme (e.g., horseradish peroxidase, β-galactosidase, luciferase, alkaline phosphatase, malate dehydrogenase, glucose oxidase, acetylcholine esterase, and catalase), a fluorophore (e.g., fluorescein isothiocyanate, dichlorotriazinyl aminofluorescein, green fluorescent protein, rhodamine, phycocyanin, fluorescamine, TEXAS RED dye (Molecular Probes), AMCA, Cy3, Cy5, and lanthanide phosphors), a chemiluminescent label (e.g., an acridinium ester), a hapten, a dye, a metal, and a metal compound. The labels can be attached directly to the monoclonal antibody or can be attached to the monoclonal antibody via spacer arms or linkers (such as $(CH_2)_n$, where n is less than about 20) of various lengths to reduce potential steric hindrance.

The monoclonal antibody can be attached to a detectable label using methods known in the art. Attachment can be accomplished by any chemical reaction that will bind the detectable marker and the antibody so long as the antibody and the marker retain their respective activities. This linkage can include many chemical mechanisms, for instance covalent binding, affinity binding, intercalation, coordinate binding and complexation. Most often, the linkage is made through covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. Representative coupling agents can include organic compounds such as thioesters, carbodiimides, N-hydroxysuccinimide esters, diisocyanates, glutaraldehyde, diazobenzenes and hexamethylene diamines. This listing is not intended to be an exhaustive compilation of the various classes of coupling agents known in the art but, rather, is representative of the more common coupling agents. (See, e.g., Killen and Lindstrom (1984), Jour. Immun. 133:1335–2549; Jansen, et al. (1982), Immunological Reviews, 62:185–216; Feltkamp et al., (1970) Immunology, 18:865–81; Nygren et al., (1979) Med. Biol., 57:187–91; Eckelman et al., (1980) Cancer Res., 40:3036–42; Westin et al., (1980) Biochim Biophys. Acta, 612: 40–49; Tijssen et al., (1984) Anal. Biochem., 136: 451–57; O'Shannessy et al., (1984) Immunol. Lett., 8:273–277; Dhawan et al., (2002) Peptides, 12:2091–98; and Elliston et al., (2000) Biotechniques, 28: 318–326). Further, commercial kits are widely available for attachment of a variety of labels to proteins, including antibodies.

The monoclonal antibodies of the invention can be attached to a linker molecule or a hapten such as biotin. Biotin has a well-known extremely high affinity for avidin and streptavidin which has been exploited in a wide variety of applications (see Bioconjugate Techniques, G. Hermanson, Academic Press, 1996). Methods and assays for the attachment of a linker to the monoclonal antibody are known in the art (see, e.g., Peranen et al., (1992) Biotechniques, 13; 456–59; Boorsma et al., (1986) Histochemistry, 84:333–337). Further, commercial kits are widely available for attachment of a variety of linkers to antibodies, for example, compounds and kits for biotinylating proteins are commercially available (e.g., N-hydroxy-succinimidylbiotin).

In addition, the monoclonal antibodies of the invention can be attached to a solid substrate, for example, by adsorption or chemical bond. The attachment of the monoclonal antibody to the solid substrate can be a direct attachment or can be an indirect attachment, for example, via a linker molecule. Examples of suitable solid substrates for direct or indirect attachment include, but are not limited to, a reagent tube, a microtiter plate, cellulose, SEPHAROSE particles (Pharmacia, Inc.), metal particles, magnetic particles, and a glass, gold, or silicon sensor surface, as well as other known and commercially available substrates. Attachment of the monoclonal antibody to the substrate can be achieved using methods described herein and otherwise well known in the art.

The present invention is also directed to hybridoma cell lines that produce the monoclonal antibodies of the invention. The hybridoma cell line can be generated using the methods described herein and otherwise known in the art. Specific examples of such hybridoma cell lines include ATCC PTA 5020, ATCC PTA 5021, ATCC PTA 5022, and ATCC PTA 5023.

Methods for Producing the Monoclonal Antibodies of the Invention

The present invention also provides methods for generating the monoclonal antibodies of the invention. In particular, the invention provides a novel method for producing monoclonal antibodies specific for one or more buprenorphine metabolites using the parent drug (i.e., buprenorphine conjugate) as an immunogen and screening for monoclonal antibodies that specifically bind the buprenorphine metabolites of interest. The method is advantageous in that a conjugate of the parent drug buprenorphine is used as an immunogen to produce monoclonal antibodies that specifically bind one or more buprenorphine metabolites, thereby eliminating the need to use a conjugate of the metabolite as an immunogen. Further, it is also possible to screen hybridomas using the parent drug buprenorphine as a screening agent to obtain hybridomas that produce monoclonal antibodies that specifically bind to one or more buprenorphine metabolites.

In one embodiment, the present invention provides a method for generating a monoclonal antibody that specifically binds buprenorphine and does not cross-react with a buprenorphine metabolite. In another embodiment, the present invention provides a method for generating a monoclonal antibody that specifically binds a buprenorphine metabolite and does not cross-react with buprenorphine or other buprenorphine metabolites. In another embodiment, the present invention provides a method for generating a monoclonal antibody that specifically binds one or more buprenorphine metabolites and does not cross-react with buprenorphine. In yet another embodiment, present invention provides a method for generating a monoclonal antibody that specifically binds buprenorphine and one or more buprenorphine metabolites.

In all of the embodiments of the inventive method, a buprenorphine conjugate is used as the immunogen. Accordingly, the method comprises administering to a mammalian subject a sufficient amount of a carrier conjugate of a buprenorphine hapten to generate an immune response in the mammalian subject; generating an immune response in the mammalian subject; isolating lymphocytes from the immunized mammalian subject; fusing the isolated lymphocytes with myeloma cells to generate hybridoma cells; screening the generated hybridoma cells using buprenorphine and/or a buprenorphine metabolite to identify hybridoma cells that produce a monoclonal antibody that specifically binds to buprenorphine and/or one or more buprenorphine metabolites; and isolating the identified monoclonal antibody that specifically binds buprenorphine. In one embodiment, the method further comprises testing the binding specificity of the isolated monoclonal antibody with buprenorphine and one or more buprenorphine metabolites to confirm the binding specificity of the monoclonal antibody.

The above-described methods employ well-established hybridoma techniques described in the art (e.g., Kohler and Milstein, Nature, 256:495–97 (1975); De St. Groth and Scheidegger, J. Immunol. Meth., 35: 1–21 (1980); E. Harlow and D. Lane, ed., "Antibodies: A Laboratory Manual", (1988), Cold Spring Harbor Laboratory, Cold Spring Harbor, N.Y.; Hammerback and Vallee, J. Biol. Chem., 265: 12763 (1990)). Briefly, an immunogen is injected into a mammalian subject so as to elicit a desired immune response in that animal. Suitable animals for immunizing include, but are not limited to, mouse, rat, guinea pig, rabbit, goat, sheep, horse, pig, dog, cat, and chicken. The immunization protocol is designed such that the dose of immunogen is sufficient to stimulate the immune system, and the injection schedule allows for the maturation of the immune response in the animal. For example, a typical immunization schedule involves a series of immunizations comprising an initial injection followed by about 1–4 booster immunizations at approximately 2- to 6-week intervals. The immunogen is usually suspended in a physiological vehicle, such as isotonic saline or phosphate buffered saline (PBS) buffer. An adjuvant, such as Freund's or RIBI adjuvant, can also be incorporated into the immunization preparation. The route of injection is typically intraperitoneal, although other routes, for example, subcutaneous, intramuscular, intravenous, and injection into the foot pad, are also effective in inducing an immune response. Antibody-producing lymphocytes are obtained from the animal either from the spleen, lymph nodes or peripheral blood using methods described herein and known in the art. Preferably, lymphocytes are obtained from the spleen. The splenic lymphocytes are then fused with a myeloma cell line, usually in the presence of a fusing agent such as polyethylene glycol (PEG), using techniques described herein and known in the art. Any number of myeloma cell lines available in the art may be used as a fusion partner according to standard techniques. Non-limiting examples of such myeloma cell lines include FO, P3, NS 1, K653, PAI and SP2/OAg14 myelomas, as well as other myeloma cells known in the art and commercially available. The resulting cells, which include the desired hybridomas, are then grown in a selective medium, for example, HAT or HTM medium. In such medium, only successfully fused hybridoma cells survive while unfused parental myeloma or lymphocyte cells die. The surviving cells are then grown under limiting conditions to obtain isolated clones, and their supernatants are screened for the presence of antibodies having a desired binding specificity using screening methods described herein and otherwise known in the art. Positive clones can be subcloned under limiting dilution conditions and the desired monoclonal antibodies isolated. Hybridomas produced according to these methods can be propagated in vitro or in vivo (e.g., in ascites fluid) and purified using common techniques known in the art. Methods for purifying monoclonal antibodies include, for example, ammonium or sodium sulfate precipitation, precipitation with polyethylene glycol, electrophoresis, gel filtration, ultracentrifugation, ion exchange chromatography, hydroxyapatite chromatography, affinity chromatography, and like methods (see, e.g., Zola et al., "Techniques for the Production and Characterization of Monoclonal Hybridoma Antibodies", in Monoclonal Hybridoma Antibodies: Techniques and Applications, pp. 51–52 (Hurell, ed., CRC Press, 1982)).

A variety of carrier conjugates of a buprenorphine hapten can be used to elicit the immune response in the above-described methods. Unexpectedly, it was found that a carrier conjugate of a buprenorphine hapten could be used as an immunogen to generate not only a monoclonal antibody that specifically binds buprenorphine, but also a monoclonal antibody that specifically binds one or more buprenorphine metabolites and is not cross-reactive with buprenorphine. Also, it was surprisingly found that a carrier conjugate of a buprenorphine hapten could be used as an immunogen to generate a monoclonal antibody that specifically binds buprenorphine and one or more buprenorphine metabolites. Suitable carrier conjugates of a buprenorphine hapten include, for example, buprenorphine-BSA and buprenorphine-KLH, as well as buprenorphine conjugates with other known carrier molecules described herein and well-established in the art. In one specific embodiment of the inventive method, the immunogen is buprenorphine-KLH having the structure:

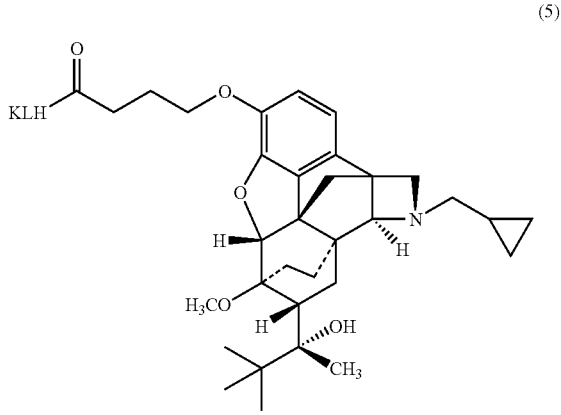

(5)

Figure 2:
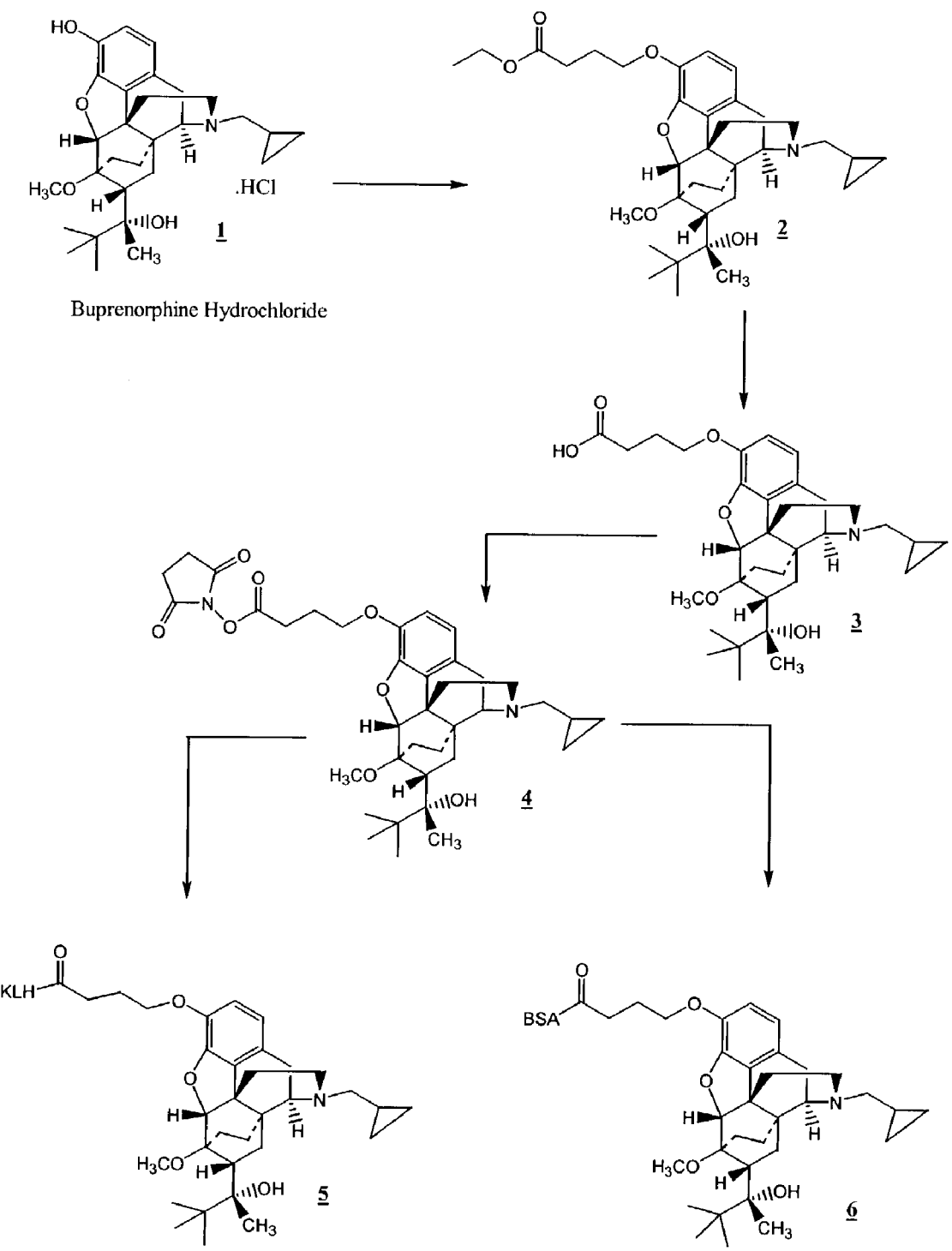
FIG. 2 is a schematic showing the synthesis of buprenorphine-BSA conjugate and buprenorphine-KLH conjugate from buprenorphine hydrochloride.

The structures of buprenorphine-BSA and buprenorphine-KLH are shown in FIG. 2. Methods for the synthesis of buprenorphine-BSA and buprenorphine-KLH are described in Example 1.

In another embodiment, a buprenorphine metabolite or conjugate thereof can be used as an immunogen to generate monoclonal antibodies that specifically bind to buprenorphine and/or one or more buprenorphine metabolites. In one embodiment, the immunogen is a buprenorphine metabolite-hapten carrier conjugate, for example, a buprenorphine glucuronide conjugate or a norbuprenorphine conjugate. Exemplary norbuprenorphine conjugates include norbuprenorphine-KLH, in which the KLH is covalently attached through a linker to the nitrogen atom (N17) of norbuprenorphine and norbuprenorphine-BSA, in which the BSA is covalently attached through a linker to the nitrogen atom (N17) of norbuprenorphine. The structures of norbuprenorphine-KLH and norbuprenorphine-BSA are shown in FIG.

4. Methods for the synthesis of norbuprenorphine-KLH and norbuprenorphine-BSA are described in Example 2.

In addition to BSA and KLH carriers, other suitable protein carriers can be used to form buprenorphine and buprenorphine metabolite immunogen conjugates, including chicken gamma globulin, ovalbumin, human thyroglobulin, bovine thyroglobulin (BTG) and other carriers known in the art. Methods for conjugation to buprenorphine or buprenorphine metabolite are known in the art and can be found in, for example, E. Harlow and D. Lane, ed., "Antibodies: A Laboratory Manual", (1988), Cold Spring Harbor Laboratory, Cold Spring Harbor, N.Y.; T. Chard in "An Introduction to Radioimmunoassay and Related Techniques", (1990), $4^{th}$ Ed., Elsevier, Amsterdam; and P. Tijssen, in "Practice and Theory of Enzyme Immunoassays", (1990), $4^{th}$ Ed., Elsevier, Amsterdam.

The hybridomas can be screened using an appropriate screening agent and standard assays described herein and otherwise known in the art to identify hybridomas that produce antibodies having the desired binding characteristics, e.g. antibodies that bind to buprenorphine and/or one or more buprenorphine metabolites. Standard immunoassays can be used as screening assays to select for hybridomas that produce the monoclonal antibodies of the invention. For example, enzyme immunoassay (EIA), enzyme-linked immunosorbant assay (ELISA), radioimmunoassay (RIA), indirect competitive immunoassay, direct competitive immunoassay, non-competitive immunoassay, sandwich immunoassay, and other immunoassays known in the art can be used with any of the screening agents described herein or any combination of screening agents described herein.

A variety of buprenorphine and buprenorphine metabolites and combinations thereof can be used as screening agents in the above-described methods. Unexpectedly, it was found that buprenorphine or a buprenorphine conjugate could be used as a screening agent to obtain not only monoclonal antibodies that specifically bind buprenorphine, but also monoclonal antibodies that specifically bind one or more buprenorphine metabolites and is not cross-reactive with buprenorphine. Also, it was surprisingly found that buprenorphine or a buprenorphine conjugate could be used as a screening agent to obtain a monoclonal antibody that specifically binds buprenorphine and one or more buprenorphine metabolites. Suitable screening agents include buprenorphine, buprenorphine metabolites (e.g., norbuprenorphine, norbuprenorphine glucuronide, and buprenorphine glucuronide), buprenorphine conjugates (e.g., buprenorphine-KLH, buprenorphine-BSA) and buprenorphine metabolite conjugates (e.g., norbuprenorphine-KLH, norbuprenorphine-BSA, norbuprenorphine glucuronide-KLH, norbuprenorphine glucuronide-BSA). The screening agent(s) can be used alone or in combination with any other screening agent.

For example, the screening assay can be a series of competitive immunoassays, such as competitive ELISAs, in which free buprenorphine is used to compete with buprenorphine bound to a solid substrate. Alternatively, the screening assay can be a competitive immunoassay, such as competitive ELISA, in which a free buprenorphine metabolite is used to compete with buprenorphine bound to a solid substrate. The screening procedure for a hybridoma can also involve two or more separate screening assays. For example, the screening assays can be competitive immunoassays, such as competitive ELISAs, in which free buprenorphine is used to compete with buprenorphine bound to a solid substrate in one assay and free buprenorphine metabolite is used to compete with buprenorphine bound to a solid substrate in another assay.

In one embodiment, a buprenorphine conjugate, such as buprenorphine-KLH or buprenorphine-BSA, is used as a screening agent alone or in combination with one or more other screening agents to select for hybridomas that produce monoclonal antibodies that specifically bind to buprenorphine and/or one or more buprenorphine metabolites.

In another embodiment, a buprenorphine metabolite conjugate can be used as a screening agent, alone or in combination with other screening agents, to select for hybridomas that produce monoclonal antibodies that specifically bind to buprenorphine and/or one or more buprenorphine metabolites. In one embodiment, a buprenorphine metabolite conjugate, such as norbuprenorphine-KLH and norbuprenorphine-BSA, is used as a screening agent alone or in combination with another screening agent. In another embodiment, the screening agent is a norbuprenorphine glucuronide conjugate, such as norbuprenorphine glucuronide-KLH and norbuprenorphine glucuronide-BSA. In another embodiment, the screening agent is a buprenorphine glucuronide conjugate.

In one embodiment, the invention provides a buprenorphine metabolite conjugate having the structure

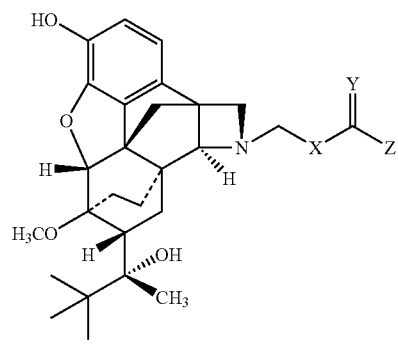

wherein X is a linking group consisting of 0–10 carbon atoms or heteroatoms including 0–2 substituted or unsubstituted aromatic rings, Y is O, NH, or S, and Z is a leaving group, poly(amino acid), protein, polysaccharide, or label.

Norbuprenorphine metabolite conjugates having the above structure are advantageous in that they are derived from a novel N-alkylated buprenorphine derivative, which structure is closer to the structure of buprenorphine than previously described N-acylated derivatives of buprenorphine. Thus, in one specific embodiment, the screening agent is a norbuprenorphine-KLH, in which the KLH is covalently attached through a linker to the nitrogen atom (N17) of norbuprenorphine. In another embodiment, the screening agent is norbuprenorphine-BSA, in which the BSA is covalently attached through a linker to the nitrogen atom (N17) of norbuprenorphine.

In one specific embodiment, the screening agent has the structure

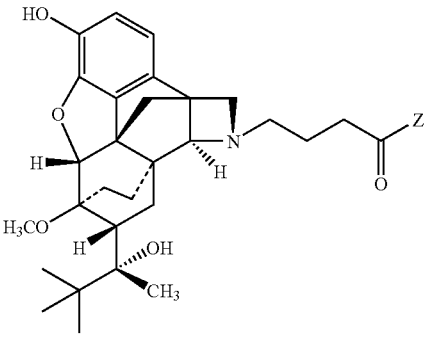

(12)

wherein Z is BSA or KLH.

The present invention provides a method for making the above compound (12), which method comprises reacting a compound of the structure:

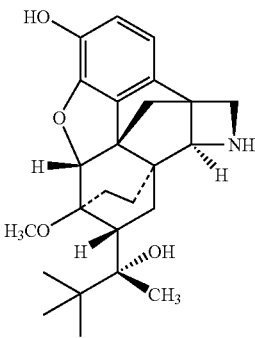

(8)

with succinic semialdehyde in the presence of a solvent and a reducing agent to form an N-alkylated compound of the structure:

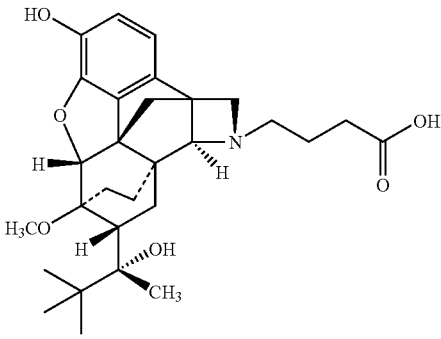

(9)

and coupling the carboxyl group of a compound of the structure (9) with KLH or BSA in the presence of a coupling reagent, and an optionally added coupling additive, and a solvent, to form the desired product of structure (12).

In one embodiment of this aspect, the reducing agent is selected from $NaBH_4$, $NaBH_3CN$, $NaBH_3(OAc)$, $Zn(BH_4)_2$, $LiBH(s-Bu_3)$, $LiBH_3[N(C_3H_7)_2]$ sodium triacetoxyborohydride, and bis(isopropoxy-titanium)borohydride.

In another embodiment of this aspect, the coupling reagent is selected from DCC (dicyclohexyl carbodiimide), DIC (1,3 diisopropyl carbodiimide), EDCI (1-ethyl-3-(3'-dimethylaminopropyl)carbodiimide hydrochloride), BBC (1-benzotriazol-1-yloxy-bis(pyrrolidino)uronium hexafluorophosphate), BDMP (5-(1H-benzotriazol-1-yloxy)-3,4-dihydro-1-methyl 2H-pyrrolium hexachloroantimonate), BOMI (benzotriazol-1-yloxy-N,N-dimethylmethaniminium hexachloroantimonate), HATU (O-(7-azabenzotriazol-1-yl)-1,1,3,3-tetramethyluronium hexafluorophosphate), HAPyU=O-(7-azabenzotriazol-1-yl)-1,1,3,3-bis(tetramethylene)uronium hexafluorophosphate, HBTU=O-(benzotriazol-1-yl)-1,1,3,3-tetramethyluronium hexafluorophosphate, TAPipU=O-(7-azabenzotriazol-1-yl)-1,1,3,3-bis(pentamethylene)uronium tetrafluoroborate, AOP (O-(7-azabenzotriazol-1-yl)-tris(dimethylamino)phosphonium hexafluorophosphate), BDP (benzotriazol-1-yl diethyl phosphate), BOP (1-benzotriazolyoxytris(dimethylamino)phosphonium hexafluorophosphate), PyAOP (7-azobenzotriazolyoxytris (pyrrolidino)phosphonium hexafluorophosphate), PyBOP (1-benzotriazolyoxytris(pyrrolidino)phosphonium hexafluorophosphate), TDBTU (2-(3,4-dihydro-4-oxo-1,2,3-benzotriazin-3-yl)-1,1,3,3-tetramethyluronium tetrafluoroborate), TNTU (2-(5-norbornene-2,3-dicarboximido)-1,1,3,3-tetramethyluronium tetrafluoroborate), TPTU (2-(2-oxo-1(2H)-pyridyl-1,1,3,3-tetramethyluronium tetrafluoroborate), TSTU (2-succinimido-1,1,3,3-tetramethyluronium tetrafluoroborate), BEMT (2-bromo-3-ethyl-4-methyl thiazolium tetrafluoroborate), BOP-Cl (bis(2-oxo-3-oxazolidinyl)phosphinic chloride), BroP (bromotris (dimethylamino)phosphonium hexafluorophosphate), BTFFH (bis(tetramethylenefluoroformamidinium) hexafluorophosphate), ClP (2-chloro-1,3-dimethylimidazolidinium hexafluorophosphate), DEPBT (3-(diethoxyphosphoryloxy)-1,2,3-benzotriazin-4(3H)-one), Dpp-Cl (diphenylphosphinic chloride), EEDQ (2-ethoxy-1-ethoxycarbonyl-1,2-dihydroquinoline), FDPP (pentafluorophenyl diphenylphosphinate), HOTT (S-(1-oxido-2-pyridinyl)-1,1,3,3-tetramethylthiouronium hexafluorophosphate), PyBroP (bromotris(pyrrolydino) phosphonium hexafluorophosphate), PyCloP (chlorotris (pyrrolydino)phosphonium hexafluorophosphate), TFFH (tetramethylfluoroformamidinium hexafluorophosphate), TOTT (S-(1-oxido-2-pyridinyl)-1,1,3,3-tetramethylthiouronium tetrafluoroborate).

In another embodiment of this aspect, the coupling additive is selected from HOBt (1-hydroxybenzotriazole), HOAt (1-hydroxy-7-azabenzotriazole), HODhbt (3-Hydroxy-3,4-dihydro-4-oxo-1,2,3-benzotriazine), (CDI) carbonyldiimidazole, NEPIS (N-ethyl-5-phenylisoxazolium-3'-sulfonate), and HOSu (N-hydroxysuccinimide).

In yet another embodiment of this aspect, the carboxy group of a compound of structure (9) is reacted with the coupling reagent and an optionally added coupling additive in a solvent selected from halogenated hydrocarbons, ethers, acetonitrile, THF, dioxane, or mixtures thereof, and the product of the above-mentioned reaction is reacted with KLH in a solvent which is a mixture of water with an optionally added buffer and one or more dipolar aprotic solvents, selected from example, from DMF, DMSO, DMPU, HMPA, acetone, and acetonitrile.

In another embodiment, an active ester of the carbosy group of a compound of structure (9) is first formed and isolated. Active esters include N-hydroxysuccinimide esters, p-nitrophenyl esters, 1-hydroxybenztriazolyl esters, and pentafluorophenyl esters. Synthesis of an N-hydroxysuccinimide ester of 3-O-carboxypropyl-buprenorphine is described in Example 1 and FIG. 2. Likewise, synthesis of an N-hydroxysuccinimide ester of N-carboxypropyl norbuprenorphine is described in Example 2 and FIG. 4.

A selected monoclonal antibody can be further tested using standard immunoassays and the above-described buprenorphine, buprenorphine metabolites, buprenorphine conjugates, and buprenorphine metabolite conjugates, as well as other test compounds, such as opiates, to determine the binding characteristics of the monoclonal antibody. For example, such compounds can be used to determine the binding specificity and/or binding affinity for buprenorphine, one or more buprenorphine metabolites, and other opiates using methods described herein (see Example 3) and otherwise known in the art. Numerous methods for determining antibody specificity and/or binding affinity employing immunoassay are known in the art. (See, for example, "Antibodies: A Laboratory Manual," Harlow and Lane (Eds.), Cold Spring Harbor Press, (1988); Friguet et al., *J. Immunol. Meth.* 77: 305–319 (1985); Muller et al., *J. Immunol. Meth.* 34: 345–352 (1980); Antoni et al., *J. Immunol. Meth.* 83:61 (1985)). The binding affinity of a monoclonal antibody can also be determined using other techniques, including mini-gel filtration technique (see, for example, Niedel, *J. Biol. Chem.* 256:9295 (1981)) and measurement of association/dissociation rates using, for example, a biosensor-based analytical system such as BIAcore (Pharmacia Biosensor AB, *Nature* 361:186–187 (1993)).

Methods for Using the Monoclonal Antibodies of the Invention

The monoclonal antibodies of the invention can be used in a method for the detection of buprenorphine and/or buprenorphine metabolites in a mammalian subject by obtaining a body fluid or tissue sample from the test subject and contacting the sample with one or more monoclonal antibodies of the invention under conditions suitable for the formation of antibody-antigen complexes. The presence or amount of such complexes is then determined by methods described herein and otherwise known in the art, in which the presence or amount of complexes found in the test sample is compared to the presence or amount of complexes found in a series of standards or control samples containing a known amount of antigen. Accordingly, the present invention further relates to methods for detecting buprenorphine and/or one or more buprenorphine metabolites in a biological sample, preferably blood, serum, urine, mucus, or saliva.

In one embodiment, the invention provides a method for detecting buprenorphine in a sample, the method comprising contacting the sample with a monoclonal antibody that specifically binds to buprenorphine and is not cross-reactive with a buprenorphine metabolite under conditions suitable for the monoclonal antibody to bind buprenorphine and detecting the buprenorphine bound to monoclonal antibody. In another embodiment, the method comprises contacting the sample with a monoclonal antibody that specifically binds to buprenorphine and one or more buprenorphine metabolites. In another embodiment, the method comprises contacting the sample with two or more monoclonal antibodies that specifically bind to buprenorphine, wherein each monoclonal antibody recognizes a different epitope.

In another embodiment, the invention provides a method for detecting a buprenorphine metabolite in a sample, which method comprises contacting the sample with a monoclonal antibody that specifically binds to one buprenorphine metabolite and is not cross-reactive with buprenorphine or another buprenorphine metabolite under conditions suitable for the monoclonal antibody to bind the buprenorphine metabolite and detecting the buprenorphine metabolite bound to monoclonal antibody. In another embodiment, the method comprises contacting the sample with two or more monoclonal antibodies that specifically bind to a buprenorphine metabolite and are not cross-reactive with buprenorphine or another buprenorphine metabolite, wherein each monoclonal antibody recognizes a different epitope on the buprenorphine metabolite molecule.

In another embodiment, the invention provides a method for detecting two or more buprenorphine metabolites in a sample comprising contacting the sample with a monoclonal antibody that specifically binds to two or more buprenorphine metabolites and is not cross-reactive with buprenorphine under conditions suitable for the monoclonal antibody to bind the buprenorphine metabolites and detecting the buprenorphine metabolites bound to monoclonal antibody. In another embodiment, the method for detecting two or more buprenorphine metabolites in a sample comprises contacting the sample with two or more monoclonal antibodies, wherein each monoclonal antibody specifically binds to a different buprenorphine metabolite and is not cross-reactive with buprenorphine.

In yet another embodiment, the invention provides a method for detecting buprenorphine and one or more buprenorphine metabolites in a sample, which method comprises contacting the sample with a monoclonal antibody that specifically binds to buprenorphine and one or more buprenorphine metabolites under conditions suitable for the monoclonal antibody to bind buprenorphine and one or more buprenorphine metabolites and detecting the buprenorphine and one or more buprenorphine metabolites bound to monoclonal antibody. In another embodiment, the invention provides a method for detecting buprenorphine and one or more buprenorphine metabolites in a sample comprising contacting the sample with two or more monoclonal antibodies, wherein each monoclonal antibody specifically binds to buprenorphine or a particular buprenorphine metabolite.

In any of the described methods for detecting buprenorphine and/or one or more buprenorphine metabolites in a biological sample, the method can be an immunoassay, for example, an enzyme immunoassay (EIA), enzyme-linked immunosorbant assay (ELISA), radioimmunoassay (RIA), indirect competitive immunoassay, direct competitive immunoassay, non-competitive immunoassay, sandwich immunoassay, agglutination assay or other immunoassay describe herein and known in the art. (See, Zola, 1987, Monoclonal Antibodies: A Manual of Techniques, pp. 147–158, CRC Press, Inc.)

Immunoassays for buprenorphine and/or one or more buprenorphine metabolites may be constructed in heterogeneous or homogeneous formats. Heterogeneous immunoassays are distinguished by incorporating a solid phase separation of bound analyte from free analyte or bound label from free label. Solid phases can take a variety of forms well known in the art, including but not limited to tubes, plates, beads, and strips. One particularly preferred form is the microtiter plate. The solid phase material may be comprised of a variety of glasses, polymers, plastics, papers, or membranes. Particularly preferred are plastics such as polystyrene. Heterogeneous immunoassays may be competitive or non-competitive, i.e., sandwich, formats.

For low molecular weight analytes such as drugs and drug metabolites, competitive formats are preferred. Competitive heterogeneous immunoassays for buprenorphine and/or one or more buprenorphine metabolites may be formatted in various ways. For example, in one format, an antibody specific for buprenorphine and/or one or more buprenorphine metabolites is immobilized on a solid phase followed by incubation with sample and buprenorphine conjugate which compete for a limited number of receptor binding sites. The unbound portion of the analyte and conjugate is then removed, and the amount of bound conjugate is measured. The amount of bound conjugate is inversely proportional to the amount of buprenorphine and/or one or more buprenorphine metabolites in the sample. A dose-response calibration curve is constructed using known amounts of the analyte using methods that are well-known in the art.

A second preferred format for the present invention involves first preparing a conjugate of a buprenorphine derivative with a macromolecular carrier substance such as a protein. The preparation of such a conjugate is described herein, e.g., in Example 1 for a buprenorphine conjugate with the carrier protein bovine serum albumin (BSA) and for a buprenorphine conjugate with the carrier protein keyhole limpet hemocyanin (KLH). Conjugates of this type may be immobilized on a solid phase of choice using covalent or passive immobilization. In Example 10, passive immobilization of norbuprenorphine-BSA conjugate on a microtiter plate is illustrated. To assay for norbuprenorphine in a sample, e.g., following preparation of the conjugate-coated plate, an antibody or other receptor is added at a predetermined optimal dilution as well as sample containing norbuprenorphine. A competition results between the solid phase bound conjugate and the buprenorphine in solution for a limited number of antibody or other receptor binding sites. After incubation, the solid phase is washed to remove unbound receptor. Finally a label is added which is used to detect the presence of bound antibody or other receptor. In the case of an ELISA assay such as described in Example 10, the label may include a secondary antibody or receptor directed against the species of the bound antibody or other receptor, e.g., rabbit anti-sheep antibody, which is conjugated to an enzyme label, e.g., horseradish peroxidase (HRP). Other enzyme labels and secondary binding substances will be readily apparent to those skilled in the art of microtiter plate ELISAs. Similarly to the first described assay format, the amount of bound analyte conjugate is inversely proportional to the amount of analyte in the sample. A dose-response calibration curve is constructed with known amounts of analyte, and the amount of analyte in the unknown sample is then correlated to the calibration curve using standard methods. The amount of bound conjugate is inversely proportional to the amount of analyte in the sample.

A preferred homogeneous microparticle immunoassay method and test kit of the present invention comprises a two-reagent system comprising ready-to-use liquid reagents for the detection of buprenorphine and/or one or more buprenorphine metabolites in serum, plasma, whole blood, urine and saliva. Kinetic interaction of microparticles in solution (KIMS) is conveniently measured using automated analyzers. In this particular assay format, an antibody specific for the particular analyte is loaded on the microparticle using covalent or passive immobilization, and the analyte derivative is linked to a macromolecule of choice such as aminodextran, which is then referred to as a drug conjugate. A competitive reaction takes place between the drug conjugate and any drug in the serum sample for binding to a limited amount of specific antibody binding sites on the microparticles. The kinetic interaction of microparticles in solution, i.e., agglutination, is induced by binding of drug conjugate to the antibody on the microparticle and is inhibited by the presence of drug in the sample. The interaction of the microparticles is measured by the absorbance of the solution, which in turn is related to the turbidity of the solution. Cross-linking of particles and drug conjugate leads to higher turbidity (higher absorbance). Free drug binding to antibody on particles results in lower absorbance (lower absorbance).

A second format for a homogeneous microparticle immunoassay method and test kit comprises ready-to-use liquid reagents for the detection of buprenorphine and/or buprenorphine metabolites in serum, plasma, whole blood, urine and saliva. Kinetic interaction of microparticles in a solution, i.e., agglutination, is conveniently measured using automated analyzers. In this assay format, a drug derivative linked to a macromolecule of choice such as bovine serum albumin is loaded on the microparticles using covalent or passive immobilization. Antibody against the specific analyte is formulated in a buffer system. A competitive reaction takes place between the drug conjugate on the microparticles and any drug present in serum sample for binding to a limited amount of specific antibody in the reaction solution. The kinetic interaction of microparticles in solution is induced by binding of drug-conjugate to the antibody and is inhibited by the presence of drug in the sample. The interaction of the microparticles is measured by the absorbance of the solution, which in turn is related to the turbidity of the solution. Cross-linking of particles and drug conjugate leads to higher turbidity (higher absorbance). Free drug binding to antibody on particles results in lower turbidity (lower absorbance).

In another immunoassay format of the present invention, a fluorescent polarization immunoassay method and test kit comprises ready-to-use liquid reagents for the detection of buprenorphine and/or one or more buprenorphine metabolites in serum, plasma, whole blood, urine and saliva, using the principle of fluorescence polarization. In this assay format, the drug derivative is tagged or labeled with a fluorophore, and the antibody against the analyte is formulated in a buffer system. A competitive reaction takes place between the drug with the fluorescence tracer and any drug in serum sample for binding to a limited amount of specific antibody in the reaction solution.

When a fluorescent molecule, or fluorophore, is irradiated with light of the proper wavelength (excitation wavelength) some of the light is emitted, although at a longer wavelength (emission wavelength). Whether or not the emitted light is polarized depends on the freedom of the fluorophore to rotate in solution. A small molecule, such as fluorescein, can rotate rapidly before light emission occurs, resulting in depolarization of the emitted light. In contrast, a fluorescent macromolecular complex, such as a fluorescein-labeled drug conjugate complexed to antibody, will rotate much more slowly. Thus, in the time frame between excitation and emission, the macromolecular complex will have rotated only very slightly, and the emitted light will be polarized. Fluorescence polarization is a reproducible function of the drug concentration and is suitable for the quantitative determination of drug concentrations in samples.

Another immunoassay format contemplated by the present invention is a homogeneous electrochemical immunoassay based on the use of electroactive labels that are inhibited when bound to an antibody or other binding receptor. The preferred electroactive labels are reversible redox labels such as bipyridyl osmium complexes. Signal amplification can be achieved by redox cycling of these mediators bioelectrocatalytically by using a redox enzyme or through the use of an interdigitated array (IDA) electrode.

The format used for the homogeneous assay is a sequential binding inhibition. The sample being assayed is mixed with the antibody or other binding receptor. If buprenorphine and/or buprenorphine metabolites are present, binding occurs. Any remaining unbound antibody/binding receptors are then mixed with the drug-labeled electroactive conjugate. The unbound drug-labeled electroactive conjugate is then measured at the electrode surface.

When no buprenorphine and/or buprenorphine metabolites are present in the sample, a greater amount of antibody or binding receptor will bind to the drug-labeled electroactive conjugate. This results in maximum inhibition of the electroactive compound. High analyte concentrations in the sample result in little or no inhibition of the electroactive compound. Therefore, there is a positive correlation between electrochemical response and analyte concentration.

In yet another immunoassay format of the present invention, the buprenorphine and/or buprenorphine metabolites present in the sample competes with drug-labeled enzyme conjugate for binding sites on antibodies which are immobilized on capillary surfaces. The unbound analyte-enzyme conjugate flows to a detection zone where the enzyme turns the substrate into electroactive product. The product is then detected electrochemically at the electrode. When buprenorphine and/or buprenorphine metabolite concentration in the sample is high, there is more analyte-enzyme conjugate left unbound to flow to the detection zone. This results in a higher concentration of electroactive product produced by enzyme conjugate and a higher current detected at the electrode. Therefore, there is a positive correlation between current detected at the electrode and analyte concentration.

Another aspect of the present invention relates to kits useful for conveniently performing the assay methods of the invention for the determination of buprenorphine and/or one or more buprenorphine metabolites in a sample. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers, or various reagents can be combined in one or more containers depending on cross-reactivity and stability of the reagents.

The reagent kit of the present invention comprises a receptor specific for buprenorphine and/or one or more buprenorphine metabolites and a conjugate comprising a ligand of buprenorphine and a non-isotopic, signal-generating moiety. The reagents may remain in liquid form or may be lyophilized. The kit can further comprise calibration and control materials useful in performing the assay. The receptor or the conjugate may be immobilized on a solid support.

The following examples further illustrate the present invention but should not be construed to limit the present invention in any way.

EXAMPLES

Example 1

Synthesis of Buprenorphine-KLH and Buprenorphine-BSA Conjugates

Preparation of Buprenorphine-KLH

The preparation of buprenorphine-KLH (5) is shown in FIG. 2. First, 3-O-(ethoxycarbonylpropyl)buprenorphine (2) was prepared. Ethyl 4-bromo butyrate (300 μL, 2.09 mmol) and $K_2CO_3$ (500 mg) followed by 2 mg of 18-crown-6 was added to a solution of 190 mg (0.37 mmol) of buprenorphine hydrochloride (Sigma Chemicals) in 12 mL of anhydrous acetone (dried and distilled over $K_2CO_3$) and 5.5 mL of anhydrous DMF. The mixture was heated to reflux under argon for 70 hours and allowed to cool to room temperature. The reaction mixture was filtered, and the filtrate was concentrated under reduced pressure. Water (40 mL) was added to the residue, and the aqueous fraction was extracted with 3×50 mL of dichloromethane. The organic fractions were combined, dried ($Na_2SO_4$), and concentrated. The residue was purified by silica gel flash column chromatography using 10% ethyl acetate in dichloromethane to give 128 mg (0.22 mmol, 58%) of 3-O-(ethoxycarbonylpropyl) buprenorphine (2).

Next, 3-O-carboxypropyl-buprenorphine (3) was synthesized. $LiOH.H_2O$ (150 mg, 3.5 mmol) was added to a suspension of 120 mg (0.21 mmol) of 3-O-(ethoxycarbonylpropyl)buprenorphine (2) in 12 mL of methanol and 6 mL of water followed by the addition of 3 mL of THF. The mixture was allowed to stir at room temperature for 18 hours and concentrated under reduced pressure. To the residue, 25 mL of water was added, and the reaction mixture was adjusted to pH 5 using 1 N HCl. The aqueous fraction was extracted with 3×50 mL of dichloromethane. The organic fractions were combined, dried ($Na_2SO_4$), and concentrated under reduced pressure. The residue was purified by preparative thin layer chromatography (silica gel 60 F254 plates, E.M. Science) using methanol-ethyl acetate mixtures to give 95 mg (0.17 mmol, 83%) of desired acid 3-O-carboxypropyl-buprenorphine (3).

3-O-(succinimido-oxycarbonyl-propyl)-buprenorphine (4) was prepared by adding 150 mg (0.78 mmol) of 1-ethyl-3(3-dimethylaminopropyl)carbodiimide hydrochloride and 150 mg (1.3 mmol) of N-hydroxysuccinimide to a solution of 88 mg (0.16 mmol) of 3-O-carboxypropyl-buprenorphine (3) in 6 mL of dichloromethane (distilled over $CaH_2$). The mixture was allowed to stir under argon for 18 hours and concentrated. The residue was purified by preparative thin layer chromatography (silica gel 60 F254 plates, E.M. Science) using ethyl acetate as eluent to give 70 mg (0.10 mmol, 68%) of the activated buprenorphine ester 3-O-(succinimido-oxycarbonyl-propyl)-buprenorphine (4).

The buprenorphine immunogen, buprenorphine-KLH (5) was prepared by adding 12 mL of dimethylsulfoxide (DMSO) dropwise to a solution containing 240 mg of keyhole limpet hemocyanin (Calbiochem) in 10.2 mL of 50 mM potassium phosphate (pH 7.5) cooled in an ice bath. The reaction temperature was maintained below room temperature. A solution of 70 mg of the buprenorphine-activated ester (4) in 2 mL of DMF was added dropwise to the protein solution. The mixture was allowed to stir at room temperature for 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each for at least 6 hours each). The protein concentration was determined to be 5.2 mg/mL using Biorad Coomassie blue protein assay (Bradford, M. *Anal. Biochem.* 72:248, 1976). A total of 37 mL of the conjugate was obtained. The extent of available lysine modification was determined to be 62% by the TNBS method (Habeeb AFSA, *Anal. Biochem.* 14:328–34, 1988).

Preparation of Buprenorphine-BSA

The preparation of buprenorphine-BSA (6) is shown in FIG. 2. A solution of 1.5 g of bovine serum albumin (BSA) in 20 mL of 50 mM potassium phosphate (pH 7.5) was cooled in an ice-bath. To the solution was added 25 mL of DMSO dropwise such that the reaction mixture was maintained below room temperature. To the protein solution was added a solution of 40 mg of buprenorphine activated ester, 3-O-(succinimido-oxycarbonyl-propyl)-buprenorphine (4), in 2 mL of anhydrous DMF dropwise. The reaction mixture was allowed to stir at room temperature for 24 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each for at least 6 hours each). The protein concentration was determined to be 20.3 mg/mL using Biorad Coomassie blue protein assay (Bradford). A total of 55 mL of the buprenorphine-BSA (6) conjugate was obtained.

Example 2

Synthesis of Norbuprenorphine-KLH and Norbuprenorphine-BSA Conjugates

Preparation of Norbuprenorphine-BSA

Figure 3:
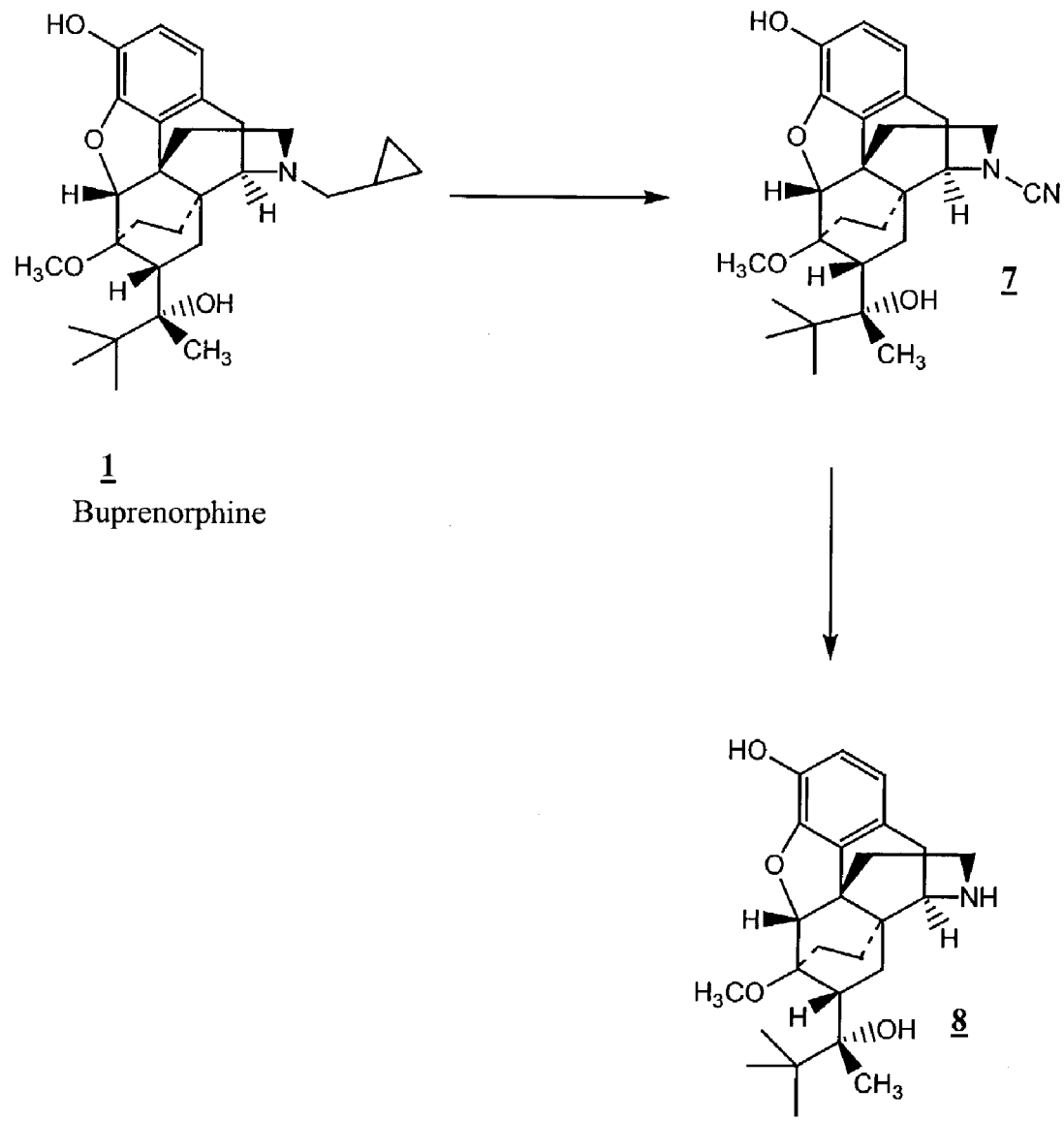
FIG. 3 is a schematic showing the synthesis of norbuprenorphine from buprenorphine.
Figure 4:
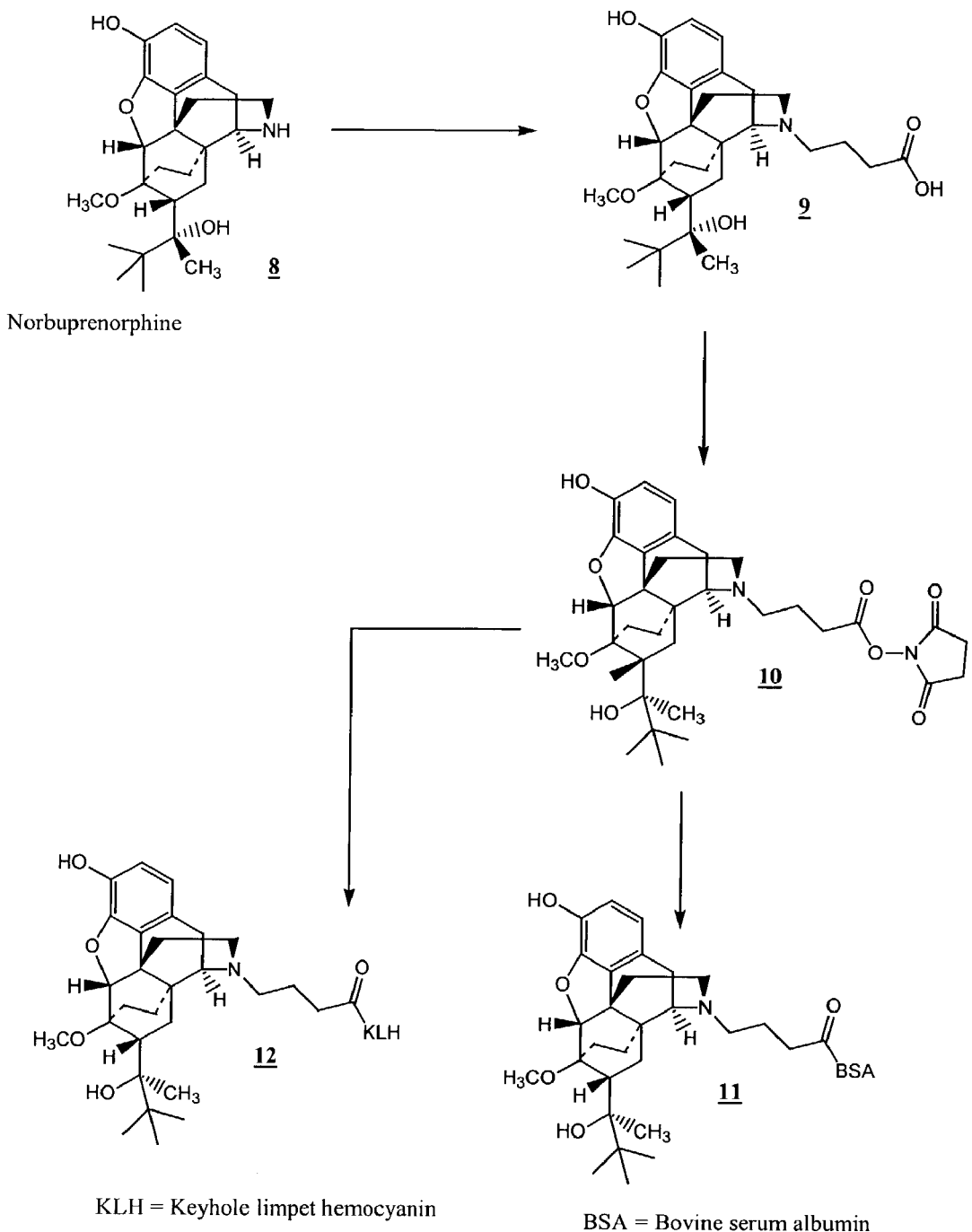
FIG. 4 is a schematic showing the synthesis of norbuprenorphine-BSA conjugate and norbuprenorphine-KLH conjugate from norbuprenorphine.

The preparation of norbuprenorphine-BSA (11) is shown in FIGS. 3 and 4. N-cyano-norbuprenorphine (7) was synthesized by converting buprenorphine hydrochloride (500 mg, 0.99 mmol) to buprenorphine free base by using aqueous potassium carbonate and extracting with dichloromethane. The organic layers were combined, dried (anhydrous $Na_2SO_4$), and concentrated. The isolated buprenorphine free base was dissolved in 10 mL of dichloromethane (distilled over $CaH_2$), and 1 mL of cyanogen bromide solution (3 M in dichloromethane) was added. The mixture was allowed to stir at 42° C. for 6 hours under argon, and 0.2 mL of cyanogen bromide solution (3 M in dichloromethane) was added. The reaction mixture was allowed to stir at 42° C. for 68 hours under argon atmosphere. The reaction mixture was concentrated and purified by preparative thin layer chromatography (silica gel 60 F254 plates, E.M. Science) using 80% chloroform in ethyl acetate to give 166 mg (38%, 0.37 mmol) of N-cyano-norbuprenorphine (7).

Norbuprenorphine (8) was prepared by adding 10 mL of glacial acetic acid, 2 mL of water, and 400 mg of Zn dust to 150 mg (0.34 mmol) of N-cyano-norbuprenorphine (7). The mixture was allowed to reflux for 2 hours, and an additional 400 mg of Zn dust was added. The mixture was heated to reflux for 7 hours and then allowed to cool to room temperature. The reaction mixture was adjusted to pH 9 by addition of 1 N NaOH. The aqueous layer was extracted with dichloromethane several times. Organic layers were combined, dried (anhydrous $Na_2SO_4$), and concentrated. The residue was purified by preparative thin layer chromatography (silica gel 60 F254 plates, E.M. Science) using a mixture of methanol and dichloromethane as eluent to give 100 mg (71%, 0.24 mmol) of norbuprenorphine (8).

A solution of 78 mg (0.18 mmol) of norbuprenorphine (8) in 4 mL of freshly distilled THF was cooled to 0° C. N-carboxypropyl-norbuprenorphine (9) was prepared by adding a solution of 0.5 mL of succinic semialdehyde (15% solution in water) in 2 mL of THF followed by 100 mg (1.59 mmol) of sodium cyanoborohydride to the norbuprenorphine reaction mixture. The mixture was allowed to stir at 0° C. for 90 minutes and at room temperature for 30 minutes. To the reaction mixture was added 1 mL of 1 N HCl, and the reaction mixture was allowed to stir for 2 hours. Solid sodium bicarbonate was added to adjust the pH of the reaction to pH 5. The reaction mixture was extracted with 3×20 mL of dichloromethane. Organic layers were combined, dried (anhydrous $Na_2SO_4$), and concentrated. The residue was purified by preparative HPLC using reverse phase C-18 column (gradient run using acetonitrile (MeCN)/$H_2O$ containing 0.1% TFA) to give 55 mg (58%, 0.11 mmol) of N-carboxypropyl-norbuprenorphine (9).

N-(succinimido-oxycarbonyl-propyl)-norbuprenorphine (10) was prepared by adding 15 μL (0.085 mmol) of diisopropylethylamine and 22 mg (0.073 mmol) of O-(N-succinimidyl)-N,N,N', N'-tetramethyluroniumtetrafluoroborate to 13.5 mg (0.027 mmol) of N-carboxypropyl-norbuprenorphine (9) in 0.7 mL of freshly distilled THF at 0° C. The mixture was allowed to warm up to room temperature and allowed to stir at room temperature for 2 hours and then concentrated. The residue was purified by preparative thin layer chromatography (silica gel 60 F254 plates, E.M. Science) using ethyl acetate as eluent to give 8 mg (0.013 mmol, 53%) of N-(succinimido-oxycarbonyl-propyl)-norbuprenorphine (10).

Norbuprenorphine-bovine serum albumin conjugate (11) was prepared as follows. A solution of 0.62 g of bovine serum albumin (BSA) in 8 mL of 50 mM potassium phosphate (pH 7.5) was cooled in an ice-bath. To the solution was added 10 mL of DMSO dropwise such that the reaction mixture was maintained below room temperature. To the protein solution was added dropwise a solution of 14 mg (0.023 mmol) of norbuprenorphine activated ester N-(succinimido-oxycarbonyl-propyl)-norbuprenorphine (10) in 1 mL of anhydrous DMF. The reaction mixture was allowed to stir at room temperature for 24 hours. The resulting conjugate was placed in a dialysis tube (10,000 MW cut-off) and was dialyzed in 1 L of 60% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each for at least 6 hours each). The protein concentration of norbuprenorphine-BSA was determined to be 21.3 mg/mL using Biorad Coomassie blue protein assay (Bradford).

Preparation of Norbuprenorphine-KLH

The preparation of norbuprenorphine-KLH (12) is shown in FIGS. 3 and 4. A solution containing 122 mg of keyhole limpet hemocyanin in 7.4 mL of 50 mM potassium phosphate (pH 7.5) was cooled in an ice-bath and add 8 mL of DMSO dropwise to the keyhole limpet hemocyanin solution such that the reaction temperature was maintained below room temperature. To the protein solution was added dropwise a solution of 32 mg of norbuprenorphine-activated ester N-(succinimido-oxycarbonyl-propyl)-norbuprenorphine (10) in 1 mL of DMF. The mixture was allowed to stir at room temperature for 42 hours. The resulting conjugate was placed in a dialysis tube (10,000 MW cut-off) and was dialyzed in 1 L of 60% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (2 L each for at least 6 hours each). The protein concentration was determined to be 3 mg/mL using Biorad Coomassie blue protein assay (Bradford). A total of 30 mL of the norbuprenorphine-KLH conjugate (12) was obtained. The extent of available lysine modification was determined to be 65% by the TNBS method (Habeeb).

Example 3

Production of Monoclonal Antibodies Using a Buprenorphine Conjugate Immunogen Immunization The buprenorphine-keyhole limpet hemocyanin (KLH) immunogen described in Example 1 was diluted to 200 µg/mL in normal saline solution. The immunogen was emulsified with an equal volume of Complete Freund's Adjuvant using a double-hubbed, 25-gauge needle and two hypodermic syringes. Female Balb/c mice 16 weeks of age or older were immunized via peritoneal injection of 0.1 mL of the emulsion. Two booster immunizations followed at intervals of at least 4 weeks.

Fusion

Four days subsequent to the third immunization, one mouse was used to produce hybridomas. The mouse was exsanguinated via retro-orbital bleeding to collect serum and subsequently cervically dislocated. The spleen was removed using aseptic technique and placed in 10 mL of complete culture medium (Iscove's Modified Dulbecco's Media, IMDM) Irvine Scientific, in a sterile petri dish. The spleen was then ground between two sterile frosted microscope slides. The resulting cell suspension was allowed to stand in a 15 mL centrifuge tube for 1–2 minutes to allow large particulates to settle. The resulting single cell suspension was drawn off and counted using a hemocytometer. FO myeloma cells (CRL-1646, American Type Culture Collection) were mixed into the spleen cells in a ratio of 1:5, FO myeloma cells:spleen cells and centrifuged for 15 minutes at about 800× G. The supernatant liquid was drawn off and discarded, and 15 mL of serum-free IMDM culture media was added. The cells were re-suspended and again centrifuged. The resulting cell pellet was fused using polyethylene glycol/DMSO according to the method of Fazekas de St. Groth (*J. Immunol. Meth.* 35:1–21, 1980).

After fusion, the cells were diluted to $2\times10^5$ splenic lymphocytes per mL in complete Iscove's Modified Dulbecco's Medium (high glucose) supplemented with 10% fetal bovine serum (Hyclone Labs), 10% Condimed HI (Roche Molecular Chemicals), 50 µM 2-mercaptoethanol, 20 µM ethanolamine, hypoxanthine-methotrexate-thymidine (all three from Sigma Chemicals, the latter diluted 1:50 for use; HMT), 4 mM glutamine and Pen/Strep antibiotics (both from Irvine Scientific). This mixture of fused cells was plated at 200 µL/well into sterile 96-well microculture plates. The covered plates were placed in an incubator for 6 days at 37° C. in 5% $CO_2$. On the sixth day, approximately 150 µL of medium was removed via an eight place vacuum manifold, and 150 µL of HT-IMDM was added. This media was prepared as above, with the exception that hypoxanthine-thymidine (Sigma, diluted 1:50; HT) was substituted for the HMT. The plates were incubated as before until visual inspection revealed growth suitable for screening (approximately 50% confluency).

Screening

The screening consisted of an enzyme-linked immunosorbant assay (ELISA) in which buprenorphine-BSA (6) or norbuprenorphine-BSA (11) was adsorbed to the plastic wells in 100 µL at a concentration of 1 µg/mL for one hour at 37° C. The wells were then rinsed with PBS-TWEEN (phosphate buffered saline with 0.05% TWEEN 20 surface active agent, ICI Americas, Inc.) and blocked with 200 µL of Post Coat Solution (1% gelatin hydrolysate, 2% sucrose in 0.15 M Tris, pH 7.2–7.4) for one hour at room temperature. The plates were then rinsed with 2% sucrose, air dried, and stored in desiccated sealed plastic bags at 4° C. until used.

The screening assay was performed as follows. Three plates coated with buprenorphine-BSA were prepared by pipetting into separate wells 50 µL of PBS-TWEEN, 50 µL of a 400 ng/mL solution of free buprenorphine in PBS-TWEEN, and 50 µL of a 400 ng/mL solution of free norbuprenorphine. A fourth plate coated with norbuprenorphine-BSA was used with 50 µL of PBS-TWEEN. Cell culture supernatant (25 µl) taken from wells showing at least 50% confluency of cell growth was diluted 1:20 in PBS-TWEEN in flexible microtiter plates (Falcon Plastics). Fifty microliters of the dilute supernatant was added to a well in each of the four microtiter plates and allowed to incubate covered at 37° C. for one hour. The plates were then washed using a Biotek Elx300 plate washer and PBS-TWEEN. Goat anti-mouse IgG-HRP (horseradish peroxidase) conjugate (Zymed Labs) was diluted 1:5,000 into PBS-TWEEN just prior to use, and 100 µL was added to all wells of all four plates. The plates were again incubated covered at 37° C. for one hour. The plates were washed as above, and 100 µL of Kblue Substrate (Neogen) was added. The color was allowed to develop for 5 minutes at room temperature in the dark. The development was halted by the addition of 100 µL of 1 N HCl (Sigma Chemicals), and color was read at 450 nm using a Molecular Devices Corp. microplate reader. Data was captured on a Macintosh computer and tabulated to show the $OD_{450}$ of each well of the different plates per culture well tested.

Selection and Sub-Cloning of Hybridomas

Hybridomas demonstrating an $OD_{450}$ greater than 1.0 in buprenorphine-BSA coated plates (containing PBS) and low $OD_{450}$ in buprenorphine-BSA coated plates containing free buprenorphine or low $OD_{450}$ in buprenorphine-BSA coated plates containing free norbuprenorphine (or low $OD_{450}$ in both competition assays) were selected for subcloning.

Selected hybridomas were immediately subjected to stringent subcloning by limiting dilution in the culture media described above. Upon growth to 25–50% confluency, the hybridomas were re-tested by the same method described above. If all subclones from a particular original fusion hybridoma provided approximately the same $OD_{450}$ results, three subclones were selected for further testing. If all wells of a particular fusion did not perform approximately equally, this was taken as evidence of instability, and three wells were used for another cycle of subcloning. This procedure was repeated until each line of hybridoma was stable. Upon stability, the cells were expanded in culture and samples were frozen at −80° in vapor-phase liquid nitrogen for storage. Samples of the culture supernatant were saved for specificity analysis.

Example 4

Production of Monoclonal Antibody Specifically Binding to Buprenorphine with No Cross-Reactivity to Buprenorphine Metabolites Hybridomas were produced, screened, and subcloned as described in Example 3. The binding specificity of the monoclonal antibody was determined using a drug competitive ELISA assay. Briefly, plates coated with either buprenorphine-BSA or norbuprenorphine-BSA at 0.1 μg/mL (other conditions as described above) were used. Antibody titer was determined from the hybridoma culture supernatants described above through assay of serial dilutions of the supernatants incubated on the coated plates. The $OD_{450}$ for each supernatant, at each dilution, was plotted versus the dilution factor. From that data, the dilution factor providing for 50–60% of the maximal $OD_{450}$ was determined. This dilution was then used for the competitive inhibition assay using the same type of plates as for the titer determination.

To prepare the competitor drugs, the following free drugs were dissolved in methanol to 1 mg/mL: (1) buprenorphine, (2) naloxone, (3) naltrexone, (4) morphine, (5) codeine, (6) oxycodone, (7) oxymorphone, (8) hydromorphone, and (9) hydrocodone. The following free drugs were dissolved in methanol to 0.1 mg/mL: (10) buprenorphine glucuronide, (11) norbuprenorphine, and (12) norbuprenorphine glucuronide. The glucuronide metabolites (10 and 12) were obtained from El Sohly Associates, all other reactants were purchased from Cerilliant (Austin, Tex.) or Alltech (Deerfield, Ill.). These stock solutions were diluted in PBS-TWEEN at a ratio of 1:333 (1) or 1:33 (2–12), and 100 μl of each transferred to row A of a microtiter plate. These solutions were serially diluted by transferring 50 μL from row A into wells of row B containing 100 μL of PBS-TWEEN and mixed by pipette. This dilution process was repeated until all eight rows of the microtiter plate contained serial dilutions of the free drug solutions.

Plates coated with either buprenorphine-BSA or norbuprenorphine-BSA at 0.1 μg/mL were prepared as described above. A 25 μL aliquot of each dilution of each free drug was transferred to a fresh conjugate-coated plate. To these solutions was added 25 μL of diluted hybridoma culture supernatant. By this procedure, 11 cross-reactants (such as the cross-reactants described above) and the drug standard, buprenorphine, were screened on a single antibody per plate. The competition assays were incubated at 37° C. for one hour. The plates were then washed using a Biotek Elx300 plate washer and PBS-TWEEN. Goat anti-mouse IgG-horseradish peroxidase (IgG-HRP) conjugate (Zymed Labs) was diluted 1:5,000 into PBS-TWEEN just prior to use, and 100 μL was added to all wells of all four plates. The plates were again incubated covered at 37° C. for one hour. The plates were washed as above, and 100 μL of Kblue Substrate (Neogen) was added. The color was allowed to develop for 5 minutes at room temperature in the dark. The development was halted by the addition of 100 μL of 1 N HCl (Sigma Chemicals), and color was read at 450 nm using a Molecular Devices Corp. microplate reader. Data was captured on a Macintosh computer. $OD_{450}$ values were graphed for each of the various concentrations of free drug competitor ($10^{-12}$–$10^{-4}$ M).

Using the testing procedures above, it was determined that buprenorphine-KLH immunogen gave rise to monoclonal antibodies that showed variable degrees of binding to buprenorphine and/or one or more metabolites. Data for antibody BUP 2.2 (FIG. 5) is typical of the results obtained by the use of a parent drug conjugate as immunogen. As shown in FIG. 5, BUP 2.2 specifically binds buprenorphine with no cross-reactivity to buprenorphine metabolites as that term is defined herein. BUP 2.2 does not cross-react with any of the other opiates listed above. $ED_{50}$ is the measure of the effective concentration of free competitor antigen (buprenorphine, buprenorphine metabolites and opiates) required to inhibit monoclonal antibody binding to substrate-bound buprenorphine by 50%. $ED_{50}$ values were as follows: buprenorphine, 1.758 nM; buprenorphine glucuronide, 49.16 nM; norbuprenorphine, 20.34 nM; and norbuprenorphine-$N_{17}$-O-glucuronide, 2.557 μM. No inhibition was observed for the other drugs tested. The data for naloxone and naltrexone were plotted merely to illustrate this point. The cross-reaction was calculated by dividing the $ED_{50}$ of the standard by the $ED_{50}$ of the drug being considered, and percent cross-reaction is calculated by multiplying the cross-reactivity by 100.

Monoclonal antibodies that specifically bind buprenorphine and have no cross-reactivity with buprenorphine metabolites (i.e., BUP 2.2) require the hydroxyl group at C3 and the N-methyl-cyclopropane at C9 for binding. Monoclonal antibodies having these binding characteristics may additionally require the tert-butyl region at C22 for binding.

Such monoclonal antibodies are clearly more suitable for use in detecting the presence of the parent compound than the metabolic products. This monoclonal antibody would not be appropriate for confirming the compliant use of buprenorphine in a subject undergoing treatment in a rehabilitation program.

TABLE 1

| | Percent Cross-Reactivity of BUP 2.2 | | | | | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 2.2 | 100 | 3.58 | 8.64 | 0.07 | 0 | 0 | 0 | 0 | 0 | 0 | 0 | 0 | 1.8e-9 |

Example 5

Production of Monoclonal Antibody Specifically Binding Buprenorphine Glucuronide Using Buprenorphine Conjugate as Immunogen Unexpectedly, it was found that an immunization program using only the parent drug conjugate (buprenorphine-KLH conjugate) gave rise to monoclonal antibodies that specifically bind to one or more buprenorphine metabolites with low cross-reactivity to buprenorphine. Thus, monoclonal antibodies that specifically bind to one or more buprenorphine metabolites can be made using a buprenorphine conjugate immunogen, which is advantageous because the parent drug is more readily available than its metabolites. Using the buprenorphine-KLH immunogen and the methods described in Example 3 to produce, screen, and subclone the hybridoma and the methods described in Example 4 to determine the binding specificity, a monoclonal antibody that specifically binds to buprenorphine glucuronide was produced.

Figure 6:
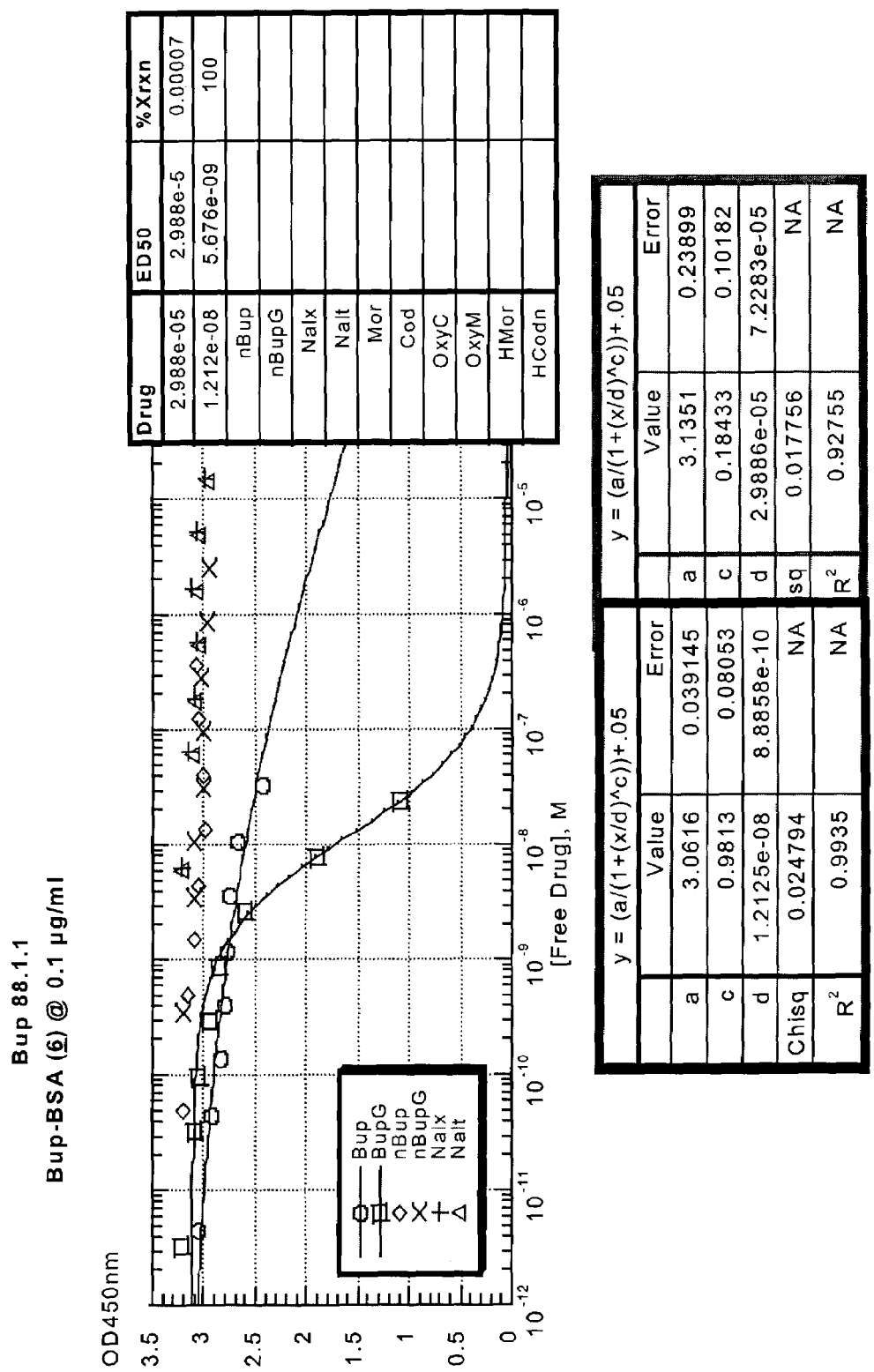
FIG. 6 is the regression plot of the data acquired in competition ELISA binding assays performed for monoclonal antibody BUP 88.1.1. The amount of monoclonal antibody BUP 88.1.1 bound to buprenorphine in the presence of various concentrations ($10^{-12}$–$10^{-4}$ M) of free opiate competitors was determined by measuring $OD_{450}$ values. Open circles show $OD_{450}$ values in the presence of various concentrations of free buprenorphine. Open squares show $OD_{450}$ values in the presence of various concentrations of free buprenorphine glucuronide. Open diamonds show $OD_{450}$ values in the presence of various concentrations of free norbuprenorphine. X's show $OD_{450}$ values in the presence of various concentrations of free norbuprenorphine $N_{17}$-O-glucuronide. Plus symbols show $OD_{450}$ values in the presence of various concentrations of free naloxone. Open triangles show $OD_{450}$ values in the presence of various concentrations of free naltrexone. $ED_{50}$ is the measure of effective concentration of free opiate competitor required to inhibit monoclonal antibody BUP 88.1.1 binding to buprenorphine by 50%. The cross-reactivity of the monoclonal antibody BUP 88.1.1 for several buprenorphine metabolites (buprenorphine glucuronide (BupG), norbuprenorphine (nBup), and norbuprenorphine glucuronide (nBupG)) relative to buprenorphine was determined by calculating $ED_{50}$ buprenorphine/$ED_{50}$ buprenorphine metabolite ×100. The monoclonal antibody did not bind to several opiates tested, including naloxone, naltrexone, morphine, codeine, oxycodone, oxymorphone, hydromorphone, and hydrocodone.

$OD_{450}$ values were determined for each of the various concentrations of free drug competitor ($10^{-12}$–$10^{-4}$ M) used in the competitor ELISA assay. As shown in FIG. 6, monoclonal antibody BUP 88.1.1 specifically binds buprenorphine glucuronide with no cross-reactivity to buprenorphine or other buprenorphine metabolites. $ED_{50}$ values are as follows: buprenorphine, 29.88 µM; buprenorphine glucuronide, 5.676 nM; norbuprenorphine, no specific binding; and norbuprenorphine-$N_{17}$-O-glucuronide, no specific binding. FIG. 6 shows that the monoclonal antibody binds buprenorphine glucuronide with a specificity about 2,500 times greater than buprenorphine. Also, BUP 88.1.1 does not cross-react with any of the other opiates listed in Example 3. The data for naloxone and naltrexone are plotted merely to illustrate this point. Monoclonal antibodies having these binding characteristics require the glucuronide group at C3 and the N-methyl-cyclopropane at C9 for binding.

Figure 9:
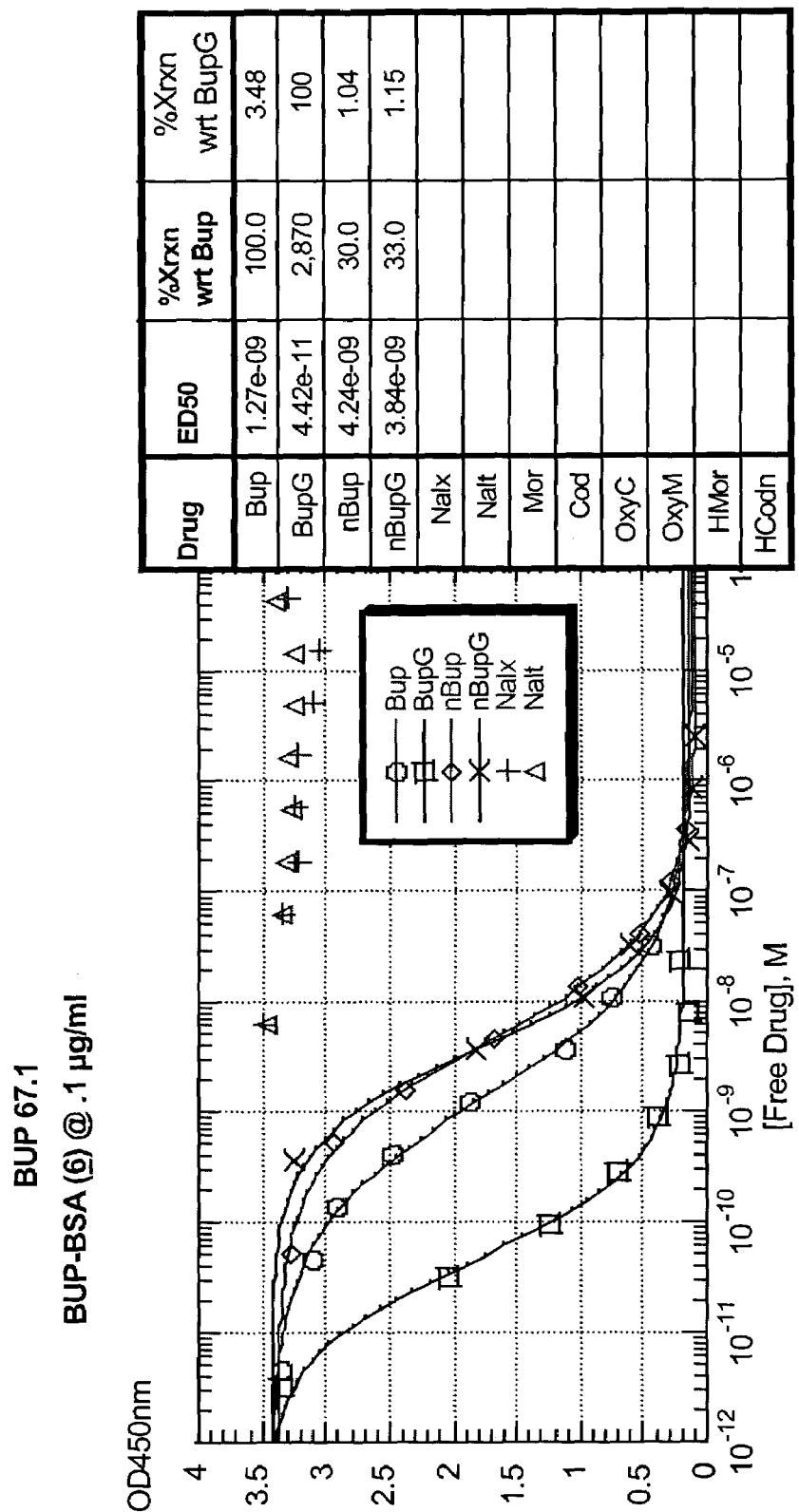
FIG. 9 is the regression plot of the data acquired in the binding assays performed for monoclonal antibody, BUP 67.1. The amount of monoclonal antibody BUP 67.1 bound to buprenorphine in the presence of various concentrations ($10^{-12}$–$10^{-4}$ M) of free opiate competitors was determined by measuring $OD_{450}$ values. Symbols for the various free competitors are as described in above in the description for FIG. 5. $ED_{50}$ is the measure of effective concentration of free opiate competitor required to inhibit monoclonal antibody BUP 67.1 binding to buprenorphine by 50%. The cross-reactivity of the monoclonal antibody BUP 67.1 for several buprenorphine metabolites (buprenorphine glucuronide (BupG), norbuprenorphine (nBup), and norbuprenorphine glucuronide (nBupG)) relative to buprenorphine was determined by calculating $ED_{50}$ buprenorphine/$ED_{50}$ buprenorphine metabolite ×100. The monoclonal antibody did not bind to several opiates tested, including naloxone, naltrexone, morphine, codeine, oxycodone, oxymorphone, hydromorphone, and hydrocodone.

Another monoclonal antibody, BUP 67.1, binds buprenorphine glucuronide with greater affinity than buprenorphine. $ED_{50}$ values are as follows: buprenorphine, 1.27 nM; buprenorphine glucuronide, 44.2 pM; norbuprenorphine, 4.24 nM; and norbuprenorphine-$N_{17}$-O-glucuronide, 3.84 nM. As shown in FIG. 9, BUP 67.1 has approximately a 30-fold higher affinity for the buprenorphine glucuronide metabolite than for the parent drug (calculated by dividing the $ED_{50}$ for the parent drug by the $ED_{50}$ for the metabolite). The monoclonal antibody has minimal cross-reactivity with norbuprenorphine metabolites.

Monoclonal antibodies having this binding specificity are suitable for detecting the presence of the buprenorphine glucuronide metabolite. Such monoclonal antibodies can be used to determine buprenorphine abuse and confirm compliance with an opiate rehabilitation program.

Example 6

Figure 7:
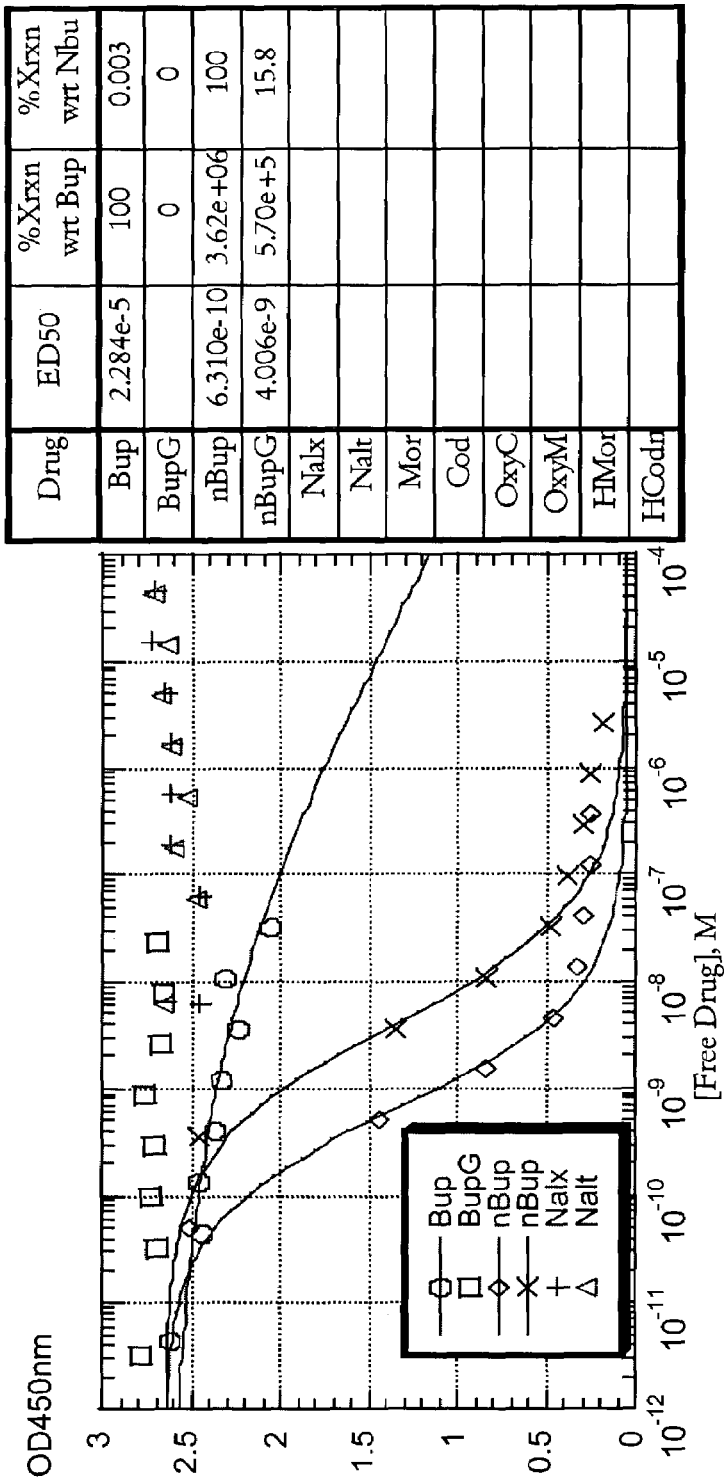
FIG. 7 is the regression plot of the data acquired in the binding assays performed for monoclonal antibody BUP 83.1.1. The amount of monoclonal antibody BUP 83.1.1 bound to buprenorphine in the presence of various concentrations ($10^{-12}$–$10^{-4}$ M) of free opiate competitors was determined by measuring $OD_{450}$ values. Symbols for the various free competitors are as described in above in the description for FIG. 5. $ED_{50}$ is the measure of effective concentration of free opiate competitor required to inhibit monoclonal antibody BUP 83.1.1 binding to buprenorphine by 50%. The cross-reactivity of the monoclonal antibody BUP 83.1.1 for several buprenorphine metabolites (buprenorphine glucuronide (BupG), norbuprenorphine (nBup), and norbuprenorphine glucuronide (nBupG)) relative to buprenorphine was determined by calculating $ED_{50}$ buprenorphine/$ED_{50}$ buprenorphine metabolite ×100. The monoclonal antibody did not bind to several opiates tested, including naloxone, naltrexone, morphine, codeine, oxycodone, oxymorphone, hydromorphone, and hydrocodone.

Production of Monoclonal Antibody Specifically Binding Norbuprenorphine Metabolites Using Buprenorphine Conjugate as Immunogen Using the buprenorphine-KLH immunogen and the methods described in Example 3 to produce, screen, and subclone the hybridoma and the methods described in Example 4 to determine the binding specificity, a monoclonal antibody that specifically binds to norbuprenorphine metabolites was isolated. $OD_{450}$ values were determined for each of the various concentrations of free drug competitor ($10^{-12}$–$10^{-4}$ M) used in the competitor ELISA assay. As shown in FIG. 7, monoclonal antibody BUP 83.1.1 specifically binds norbuprenorphine and norbuprenorphine-$N_{17}$-O-glucuronide with no cross-reactivity to buprenorphine. $ED_{50}$ values are as follows: buprenorphine, 22.84 µM; buprenorphine glucuronide, no specific binding; norbuprenorphine, 631.0 pM; and norbuprenorphine glucuronide, 4.006 nM. Specifically, antibody BUP 83.1.1 was found to have a 36,000-fold greater affinity for norbuprenorphine than for the parent drug (calculated by dividing the $ED_{50}$ for the parent drug by the $ED_{50}$ for the metabolite). BUP 83.1.1 also has no cross-reactivity with the buprenorphine glucuronide metabolite and low cross-reactivity with norbuprenorphine glucuronide. Another monoclonal antibody (BUP 42.1) demonstrated similar binding characteristics, i.e., it specifically binds to norbuprenorphine with no cross-reactivity to buprenorphine or buprenorphine glucuronide and low cross-reactivity to norbuprenorphine glucuronide. Neither BUP 83.1.1 nor BUP 42.1 cross-reacts with any of the other opiates listed in Example 3. Monoclonal antibodies sharing these binding characteristics require the absence of all or part of the N-methyl-cyclopropane group at C9 and prefer the hydroxyl group at C3 over the glucuronide group for binding.

Monoclonal antibodies having this binding specificity are suitable for detecting the presence of the norbuprenorphine metabolite. Such monoclonal antibodies can be used to confirm compliance with an opiate rehabilitation program.

Example 7

Figure 8:
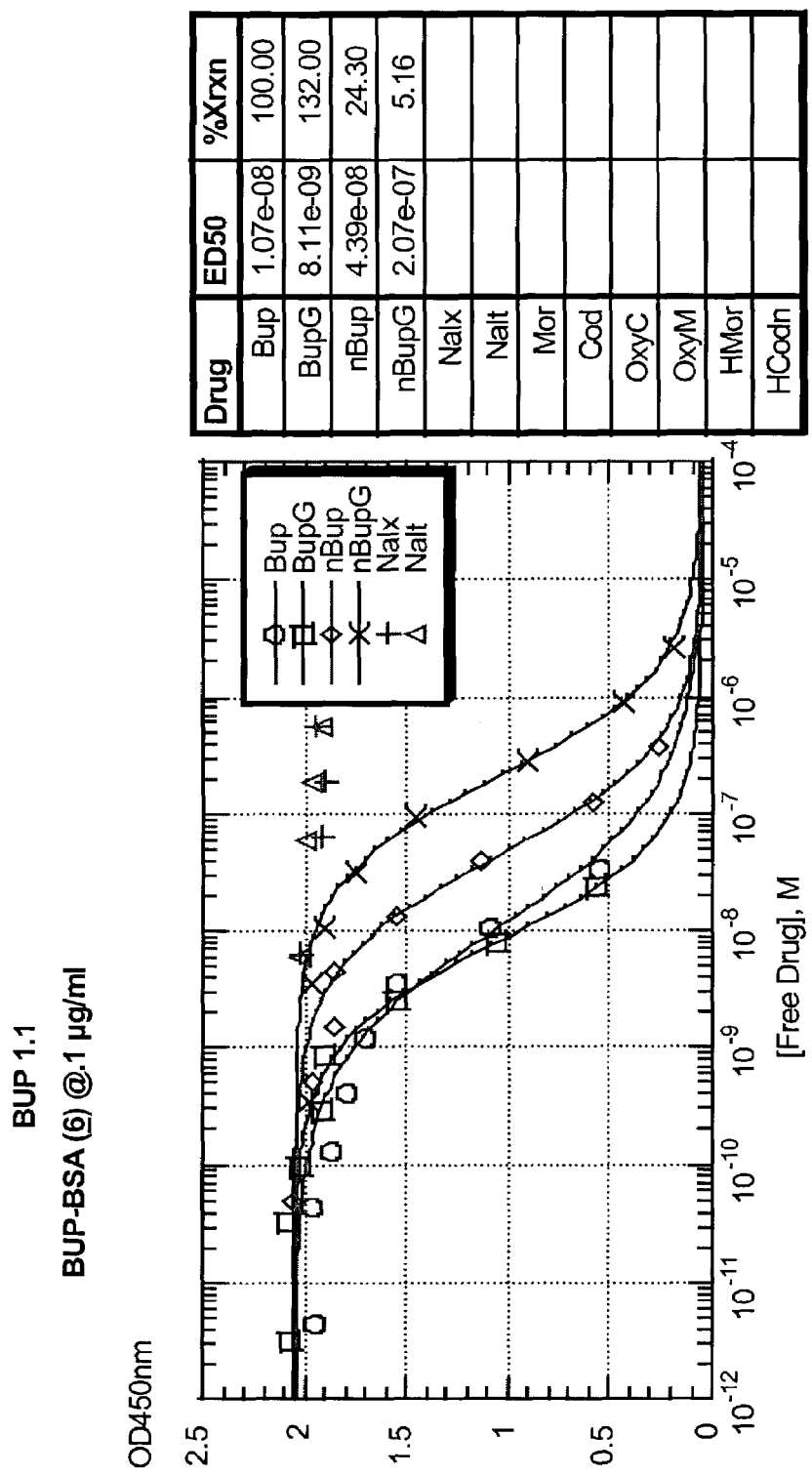
FIG. 8 is the regression plot of the data acquired in the binding assays performed for monoclonal antibody, BUP 1.1. The amount of monoclonal antibody BUP 1.1 bound to buprenorphine in the presence of various concentrations ($10^{-12}$–$10^{-4}$ M) of free opiate competitors was determined by measuring $OD_{450}$ values. Symbols for the various free competitors are as described in above in the description for FIG. 5. $ED_{50}$ is the measure of effective concentration of free opiate competitor required to inhibit monoclonal antibody BUP 1.1 binding to buprenorphine by 50%. The cross-reactivity of the monoclonal antibody BUP 1.1 for several buprenorphine metabolites (buprenorphine glucuronide (BupG), norbuprenorphine (nBup), and norbuprenorphine glucuronide (nBupG)) relative to buprenorphine was determined by calculating $ED_{50}$ buprenorphine/$ED_{50}$ buprenorphine metabolite ×100. The monoclonal antibody did not bind to several opiates tested, including naloxone, naltrexone, morphine, codeine, oxycodone, oxymorphone, hydromorphone, and hydrocodone.

Production of Monoclonal Antibody Specifically Binding Buprenorphine and Buprenorphine Glucuronide with Approximately Equal Affinity Using Buprenorphine Conjugate as Immunogen Unexpectedly, it was found that an immunization program using only the parent drug conjugate (buprenorphine conjugate) gave rise to monoclonal antibodies that cross-react to one or more metabolites with approximately the same specificity as to the homologous parent drug. Using the buprenorphine-KLH immunogen and the methods described in Example 3 to produce, screen, and subclone the hybridoma and the methods described in Example 4 to determine the binding specificity, a monoclonal antibody that specifically binds to both buprenorphine and buprenorphine glucuronide was isolated. $OD_{450}$ values were determined for each of the various concentrations of free drug competitor ($10^{-12}$–$10^{-4}$ M) used in the competitor ELISA assay. As shown in FIG. 8, monoclonal antibody BUP 1.1 binds buprenorphine and its buprenorphine glucuronide with approximately equal affinity and with low cross-reactivity with norbuprenorphine metabolites. $ED_{50}$ values are as follows: buprenorphine, 10.7 nM; buprenorphine glucuronide, 8.11 nM; norbuprenorphine, 43.9 nM; and norbuprenorphine-$N_{17}$-O-glucuronide, 207 nM. BUP 1.1 does not cross-react with any of the other opiates listed in Example 3. Table 2 shows additional monoclonal antibodies that bind buprenorphine and buprenorphine glucuronide with similar affinity and that have low cross-reactivity with norbuprenorphine metabolites. Monoclonal antibodies having these binding characteristics demonstrate partial recognition of the C3 oxygen and partial recognition of the N-methyl-cyclopropane group at C9 for binding.

TABLE 2

| | Percent cross-reactivity | | | | | | | | | | | | |
| --- | --- | --- | --- | --- | --- | --- | --- | --- | --- | --- | --- | --- | --- |
| Clone | Bup | BupG | nBup | nBupG | Nalx | Nalt | Mor | Cod | OxyC | OxyM | HMor | Hcod | $ED_{50}$ |
| 1.1 | 100 | 132 | 24.3 | 5.16 | 0 | 0 | 0 | 0 | 0 | 0 | 0 | 0 | 1e-8 |
| 3.3 | 100 | 186 | 11 | 3.4 | 0 | 0 | 0 | 0 | 0 | 0 | 0 | 0 | 6e-10 |

TABLE 2-continued

| | | | | | Percent cross-reactivity | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 26.3 | 100 | 521 | 32.2 | 20.9 | 0 | 0 | 0 | 0 | 0 | 0 | 0 | 0 | 8.5e-8 |
| 46.1 | 100 | 51.7 | 19.4 | 13.3 | 0 | 0 | 0 | 0 | 0 | 0 | 0 | 0 | 3e-9 |
| 68.1.1 | 100 | 85.5 | 18.3 | 12.9 | 0 | 0 | 0 | 0 | 0 | 0 | 0 | 0 | 2.5e-9 |

In addition, Table 3 shows monoclonal antibodies that bind buprenorphine and buprenorphine glucuronide with similar affinity and that have no cross-reactivity with nor-buprenorphine metabolites or other opiates. Monoclonal antibodies having these binding characteristics demonstrate partial recognition of the C3 oxygen and require the presence of the N-methyl-cyclopropane group at C9 for binding.

TABLE 3

| | | | | | Percent Cross-Reactivity | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 8.1 | 100 | 426 | 5.58 | 3.41 | 0 | 0 | 0 | 0 | 0 | 0 | 0 | 0 | 3.9e-9 |
| 16.3 | 100 | 429 | 0 | 0 | 0 | 0 | 0 | 0 | 0 | 0 | 0 | 0 | 6e-9 |
| 20.3 | 100 | 81 | 3.07 | 1.75 | 0 | 0 | 0 | | 0 | 0 | 0 | 0 | 1.2e-9 |
| 21.3 | 100 | 460 | 2.88 | 3.09 | 0 | 0 | 0 | 0 | 0 | 0 | 0 | 0 | 3.3e-9 |
| 23.1 | 100 | 119 | 2.05 | 1.3 | 0 | 0 | 0 | 0 | 0 | 0 | 0 | 0 | 6.8e-10 |
| 29.2 | 100 | 57.8 | 0 | 0 | 0 | 0 | 0 | 0 | 0 | 0 | 0 | 0 | 2e-11 |
| 33.1 | 100 | 323 | 0 | 0 | 0 | 0 | 0 | 0 | 0 | 0 | 0 | 0 | 3e-10 |
| 34.1.1 | 100 | 352 | 4.7 | 3.6 | 0 | 0 | 0 | 0 | 0 | 0 | 0 | 0 | 1e-9 |
| 35.1 | 100 | 186 | 0 | 0 | 0 | 0 | 0 | 0 | 0 | 0 | 0 | 0 | 2.3e-10 |
| 38.1 | 100 | 186 | 0 | 0 | 0 | 0 | 0 | 0 | 0 | 0 | 0 | 0 | 2.3e-10 |
| 56.3 | 100 | 468 | 0 | 0 | .009 | 0.02 | 0 | 0 | 0 | 0 | 0 | 0 | 2.2e-9 |
| 73.2 | 100 | 112 | 0 | 0 | 0 | 0 | 0 | 0 | 0 | 0 | 0 | 0 | 3e-11 |

Monoclonal antibodies having the binding specificity described in this example are suitable for detecting the presence of buprenorphine and its buprenorphine glucuronide metabolite. This antibody could be useful in detecting buprenorphine abuse. However, given the high cross-reactivity between buprenorphine and buprenorphine glucuronide, it would not be useful for confirming compliance with an opiate rehabilitation program due to the possibility of sample adulteration with the parent drug.

Example 8

Production of Monoclonal Antibody Specifically Binding Buprenorphine Glucuronide and Having Low Cross-Reactivity with Buprenorphine Using Buprenorphine Conjugate as Immunogen Using the buprenorphine-KLH immunogen and the methods described in Examples 3 and 4, monoclonal antibodies that specifically bind to buprenorphine glucuronide and have low cross-reactivity with buprenorphine were produced. $OD_{450}$ values were determined for each of the various concentrations of free drug competitor ($10^{-12}$–$10^{-4}$ M) used in the competitor ELISA assay. The monoclonal antibodies shown in Table 4 bind buprenorphine glucuronide with greater affinity than buprenorphine. While clones BUP 5.1, BUP 6.1, BUP 11.2, BUP 13.1.3, BUP 22.3, BUP 52.1.1, BUP 58.2.1, BUP 74.1.3, BUP 79.1, and BUP 89.2 are cross-reactive with buprenorphine, clones BUP 10.2, BUP 14.2, BUP 15.3, BUP 30.1, BUP 40.3, and BUP 66.2 are not technically cross-reactive with buprenorphine, as that term has been defined herein. The monoclonal antibodies have no cross-reactivity with norbuprenorphine metabolites. Another monoclonal antibody (BUP 4.2) demonstrated similar binding characteristics, i.e., it specifically binds to buprenorphine glucuronide with greater affinity than buprenorphine and has minimal cross-reactivity to norbuprenorphine metabolites. None of the monoclonal antibodies described in Table 4 cross-react with any of the other opiates listed in Example 3. Monoclonal antibodies having these binding characteristics require the presence of glucuronide at C3 and demonstrate partial or complete recognition of the N-methyl-cyclopropane group at C9 for binding.

TABLE 4

| | | | | | Percent Cross-Reactivity | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 5.1 | 100 | 556 | 0 | 0 | 0 | 0 | 0 | 0 | 0 | 0 | 0 | 0 | 8.2e-10 |
| 6.1 | 100 | 927 | 0 | 0 | 0 | 0 | 0 | 0 | 0 | 0 | 0 | 0 | 4.5e-8 |
| 10.2 | 100 | 1,130 | 0 | 0 | 0 | 0 | 0 | 0 | 0 | 0 | 0 | 0 | 4.7e-9 |
| 11.2 | 100 | 695 | 0.06 | 0.08 | 0.005 | 0.01 | 0 | 0 | 0 | 0 | 0 | 0 | 1.1e-9 |
| 13.1.3 | 100 | 875 | 0 | 0 | 0.013 | 0.067 | 0 | 0 | 0 | 0 | 0 | 0 | 1e-9 |

TABLE 4-continued

| | | | | | Percent Cross-Reactivity | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 14.2 | 100 | 1,330 | 0 | 0 | 0.002 | 0.08 | 0 | 0 | 0 | 0 | 0 | 0 | 5.3e-8 |
| 15.3 | 100 | 2,480 | 0 | 0 | 0 | 0 | 0 | 0 | 0 | 0 | 0 | 0 | 2.2e-7 |
| 22.3 | 100 | 852 | 0 | 0 | 0 | 0 | 0 | 0 | 0 | 0 | 0 | 0 | 2.8e-10 |
| 30.1 | 100 | 2600 | 0 | 0 | 0 | 0 | 0 | 0 | 0 | 0 | 0 | 0 | 3e-8 |
| 40.3 | 100 | 1,090 | 0 | 0 | 0 | 0 | 0 | 0 | 0 | 0 | 0 | 0 | 1.4e-8 |
| 52.1.1 | 100 | 650 | 0 | 0.1 | 0.02 | 0.06 | 0 | 0 | 0 | 0 | 0 | 0 | 9.6e-9 |
| 58.2.1 | 100 | 907 | 0 | 0 | 0 | 0 | 0 | 0 | 0 | 0 | 0 | 0 | 6.3e-9 |
| 66.2 | 100 | 1,080 | 0 | 0 | 0.03 | 0.01 | 0 | 0 | 0 | 0 | 0 | 0 | 1.7e-8 |
| 74.1.3 | 100 | 569 | 0 | 0 | 0 | 0 | 0 | 0 | 0 | 0 | 0 | 0 | 4.8e-11 |
| 79.1 | 100 | 708 | 0 | 0 | 0 | 0 | 0 | 0 | 0 | 0 | 0 | 0 | 1e-10 |
| 89.2 | 100 | 642 | 0 | 0 | 0 | 0 | 0 | 0 | 0 | 0 | 0 | 0 | 1.7e-10 |

Example 9

Production of a Monoclonal Antibody Specifically Binding Buprenorphine and Cross-Reacting with Norbuprenorphine Using Buprenorphine Conjugate as Immunogen Using the buprenorphine-KLH immunogen and the methods described in Examples 3 and 4, monoclonal antibodies that specifically bind to buprenorphine and that cross-react with norbuprenorphine were produced as shown in Table 5. The monoclonal antibodies do not cross-react with buprenorphine glucuronide metabolites or other opiates. Monoclonal antibodies having these binding characteristics require the hydroxyl at C3 and recognize the N-methylcyclopropane group at C9 for binding.

TABLE 5

| | | | | | Percent Cross-Reactivity | | | | | | | | |
|---|---|---|---|---|---|---|---|---|---|---|---|---|---|
| Clone | Bup | BupG | nBup | nBupG | Nalx | Nalt | Mor | Cod | OxyC | OxyM | HMor | Hcod | $ED_{50}$ |
| 12.2 | 100 | 3.53 | 16.8 | 0.21 | 0 | 0 | 0 | 0 | 0 | 0 | 0 | 0 | 42.3e-9 |
| 64.1.1.3 | 100 | 0 | 12.7 | 0.04 | 0 | 0 | 0 | 0 | 0 | 0 | 0 | 0 | 1.7e-8 |

Example 10

ELISA Assay for Norbuprenorphine

An ELISA assay for determining the norbuprenorphine in urine may be performed by absorbing a suitable amount of norbuprenorphine-BSA conjugate to the walls of wells in a 96-well microtiter plate. This is done by diluting the norbuprenorphine-BSA conjugate in a 0.1 M bicarbonate buffer, pH 9.4, and incubating 100 µL of the resulting solution in covered wells for at least one hour at 37° C. The unabsorbed conjugate is removed from the wells by washing and a blocking solution is added comprising 1 mg/mL of bovine serum albumin diluted in a phosphate buffered saline solution, pH 7.2–7.4. Following incubation as above for an additional hour, excess blocking solution is washed from the wells.

An assay is carried out by first establishing a standard curve for norbuprenorphine by preparing dilutions of varying known amounts of norbuprenorphine in normal human urine. These reference standards are each then diluted in PBS buffer. A buffer containing a predetermined amount of monoclonal antibody BUP 83.1.1 labeled with horseradish peroxidase is then prepared BUP 83.1.1-HRP). Such a labeled conjugate may be readily prepared using kits commercially available for linking antibodies to HRP. Samples of urine to be tested for the presence and/or amount of norbuprenorphine are likewise diluted in PBS buffer.

Fifty microliters of each of the norbuprenorphine standards and 50 µL of each of the diluted patient urine samples are then pipetted into different wells of the antibody-coated microtiter plate. Each well then receives an equal volume BUP 83.1.1-HRP solution. The plate is covered and incubated for one hour at 37° C., after which time the wells are washed with plain PBS buffer six times. The wells are then filled with 50 µL of an enzyme substrate such as Kblue (Neogene Corp.). The substrate is allowed to react in the wells for a set period of time, after which the reaction is terminated by addition of an equal volume of 1 N hydrochloric acid. The color intensity of each well is measure using a microplate reader equipped with filters for 405 nanometers.

A standard curve for norbuprenorphine is derived by plotting the intensity of color versus the amount of norbuprenorphine in each of the standard solutions. The concentration of norbuprenorphine in a diluted patient sample can then be determined by comparing the results obtained for the unknown samples with those obtained for the reference solutions.

All of the references cited herein, including patents and publications, are hereby incorporated in their entireties by reference. The methods and compositions described herein as presently representative of preferred embodiments are exemplary and are not intended as limitations on the scope of the invention. While the invention has been described with an emphasis upon preferred aspects of the invention, it will be readily apparent to those of ordinary skill in the art that variations of the preferred embodiments can be used without departing from the scope and spirit of the invention and that it is intended that the invention can be practiced otherwise than is specifically described herein. Accordingly, the present invention includes all modifications encompassed within the spirit and scope of the invention as defined by the description and the appended claims.

What is claimed is:

1. A monoclonal antibody that specifically binds buprenorphine and that has less than 10% cross-reactivity to buprenorphine glucuronide, norbuprenorphine, and norbuprenorphine glucuronide.

2. A cell line that produced a monoclonal antibody that specifically binds buprenorphine and that has less than 10% cross-reactivity to buprenorphine glucuronide, norbuprenorphine, and norbuprenorphine glucuronide.

3. Hybridoma cell line BUP 2.2 having ATCC accession number PTA 7198 and producing an antibody according to claim 1.

4. A method for determining buprenorphine in a sample comprising
   a. forming a reaction mixture comprising the sample, a monoclonal antibody that binds specifically with buprenorphine with less than 10% cross-reactivity to buprenorphine glucuronide, norbuprenorphine, and norbuprenorphine glucuronide to form a buprenorphine-antibody complex, and an buprenorphine analog conjugate that competes with the buprenorphine in the sample to form a buprenorphine analog-antibody complex, wherein either the antibody or the analog conjugate is bound to a label that combines with either the buprenorphine or the antibody, respectively, to produce a detectable signal, and
   b. determining the signal produced in step (a) as a measure of the buprenorphine in the sample.

5. The method of claim 4 wherein if the antibody is bound to the label, then the analog conjugate is bound to a solid phase, or if the analog conjugate is bound to the label, then the antibody is bound to a solid phase.

6. A monoclonal antibody that specifically binds buprenorphine glucuronide and that has essentially no cross-reactivity to buprenorphine, norbuprenorphine, and norbuprenorphine glucuronide.

7. A cell line that produces a monoclonal antibody that specifically binds buprenorphine glucuronide and that has essentially no cross-reactivity to buprenorphine, norbuprenorphine, and norbuprenorphine glucuronide.

8. Hybridoma cell like BUP 88.1.1 having ATCC accession number PTA 5023 and producing an antibody according to claim 6.

9. A method for determining buprenorphine glucuronide in a sample comprising
   a. forming a reaction mixture comprising the sample, a monoclonal antibody that binds specifically with buprenorphine glucuronide and that has essentially no cross-reactivity to buprenorphine, norbuprenorphine, and norbuprenorphine glucuronide to form a buprenorphine glucuronide-antibody complex, and a buprenorphine glucuronide analog conjugate that competes with the buprenorphine glucuronide in the sample to form a buprenorphine analog-antibody complex, wherein either the antibody or the analog conjugate is bound to a label that combines with either the buprenorphine glucuronide or the antibody, respectively, to produce a detectable signal, and
   b. determining the signal produced in step (a) as a measure of buprenorphine glucuronide in the sample.

10. The method of claim 9 wherein if the antibody is bound to the label, then the analog conjugate is bound to a solid phase, or if the analog conjugate is bound to the label, then the antibody is bound to a solid phase.

11. A norbuprenorphine conjugate having the structure:

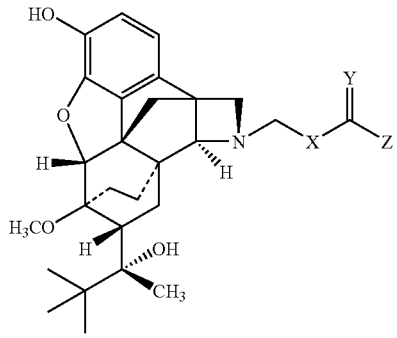

wherein X is a linking group consisting of 0–10 carbon atoms or heteroatoms including 0–2 substituted or unsubstituted aromatic rings, Y is O, NH, or S, and Z is a leaving group, poly(amino acid), protein, polysaccharide, or label.

12. The conjugate of claim 11 wherein X is $(CH_2)_2$ and Y is O.

* * * * *